(12) United States Patent
Okamitsu et al.

(10) Patent No.: US 7,401,943 B2
(45) Date of Patent: Jul. 22, 2008

(54) SOLID-STATE LIGHT SOURCES FOR CURING AND SURFACE MODIFICATION

(75) Inventors: Jeffrey Okamitsu, Westminster, MD (US); Miodrag Cekic, Bethesda, MD (US); Boris Geller, Germantown, MD (US); Mark W. Ruckman, Mongomery Village, MD (US)

(73) Assignee: Fusion UV Systems, Inc., Gaithersburg, MD (US)

( * ) Notice: Subject to any disclaimer, the term of this patent is extended or adjusted under 35 U.S.C. 154(b) by 62 days.

(21) Appl. No.: 11/146,018

(22) Filed: Jun. 7, 2005

(65) Prior Publication Data

US 2006/0274421 A1 Dec. 7, 2006

(51) Int. Cl.
*B60Q 1/26* (2006.01)

(52) U.S. Cl. ..................................... 362/227

(58) Field of Classification Search ............... 362/227, 362/237, 241, 297, 247, 245, 243, 271, 272
See application file for complete search history.

(56) References Cited

U.S. PATENT DOCUMENTS

| 4,845,481 | A | | 7/1989 | Havel |
| 4,915,489 | A | * | 4/1990 | Minko ..................... 359/834 |
| 5,161,879 | A | | 11/1992 | McDermott |
| 5,169,675 | A | | 12/1992 | Bartoszek-Loza et al. |
| 5,184,114 | A | | 2/1993 | Brown |
| 5,395,769 | A | | 3/1995 | Arienzo et al. |
| 5,420,482 | A | | 5/1995 | Phares |
| 5,420,768 | A | | 5/1995 | Kennedy |
| 5,633,629 | A | * | 5/1997 | Hochstein ................ 340/907 |
| 5,890,794 | A | | 4/1999 | Abtahi et al. |
| 6,016,038 | A | | 1/2000 | Mueller et al. |
| 6,095,661 | A | | 8/2000 | Lebens et al. |
| 6,127,447 | A | | 10/2000 | Mitry et al. |
| 6,150,774 | A | | 11/2000 | Mueller et al. |
| 6,211,626 | B1 | | 4/2001 | Lys et al. |

(Continued)

FOREIGN PATENT DOCUMENTS

DE            702 556            2/1941

(Continued)

OTHER PUBLICATIONS

PCT International Search Report and Written Opinion in International Application No. PCT/US2006/021882 (Oct. 19, 2006) (9 pages).

(Continued)

*Primary Examiner*—Renee S Luebke
*Assistant Examiner*—Vanessa Girardi
(74) *Attorney, Agent, or Firm*—Finnegan, Henderson, Farabow, Garrett & Dunner, LLP

(57) ABSTRACT

The systems and methods described herein relate to solid-state light sources capable of generating radiation beams for, but not limited to, the treatment of surfaces, bulk materials, films, and coatings. The solid-state ultraviolet source optically combines the light output of at least two and preferably as many four independently controllable discrete solid-state light emitters to produce a light beam that has a controllable multi-wavelength spectrum over a wide range of wavelengths (i.e. deep UV to near-IR). Specific features of this light source permit changes in the spectral, spatial and temporal distribution of light for use in curing, surface modification and other applications.

46 Claims, 23 Drawing Sheets

U.S. PATENT DOCUMENTS

| | | |
|---|---|---|
| 6,331,111 B1 | 12/2001 | Cao |
| 6,758,582 B1 * | 7/2004 | Hsiao et al. .................. 362/302 |
| 2001/0032985 A1 | 10/2001 | Bhat et al. |
| 2002/0017844 A1 | 2/2002 | Parkyn et al. |
| 2002/0191394 A1 | 12/2002 | Coleman et al. |
| 2004/0165381 A1 | 8/2004 | Waters |
| 2004/0213017 A1 | 10/2004 | Chou et al. |
| 2005/0024878 A1 * | 2/2005 | Holten ....................... 362/296 |
| 2005/0099108 A1 | 5/2005 | Hofmann et al. |
| 2005/0151489 A1 * | 7/2005 | Lys et al. .................... 315/308 |

FOREIGN PATENT DOCUMENTS

| | | |
|---|---|---|
| EP | 0 780 104 B1 | 12/2001 |
| WO | WO 01/24583 | 4/2001 |

OTHER PUBLICATIONS

Taniyasu, Yoshitaka et al, An Aluminum Nitride Light-Emitting Diode With a Wavelength of 210 Nanometres, Nature, May 18, 2006, vol. 441, pp. 325-328.

Hirayama, H., Et Al. "Efficient 230-280 nm emission from high-AL-content AlGaN-based multiquantum wells," Applied Physics Letters, vol. 80, pp. 37-39, Jan. 7, 2002.

Hirayama, H., et al. "Marked enhancement of 320-360 nm ultraviolet emission in quaternary $In_xAl_yGa_{1-x-y}N$ with in-segregation effect," Applied Physics Letters, vol. 80, pp. 207-209, Jan. 14, 2002.

Hirayama, H., et al. "Room-temperature intense 320 nm band ultraviolet emission from quaternary InAlGaN-based multiple-quantum wells," Applied Physics Letters, vol. 80, pp. 1589-91, Mar. 4, 2002.

Nakamura, S., et al. "The Blue Laser Diode—The Complete Story" Second Revised and Enlarged Edition, (Springer, Berlin, 2000).

* cited by examiner

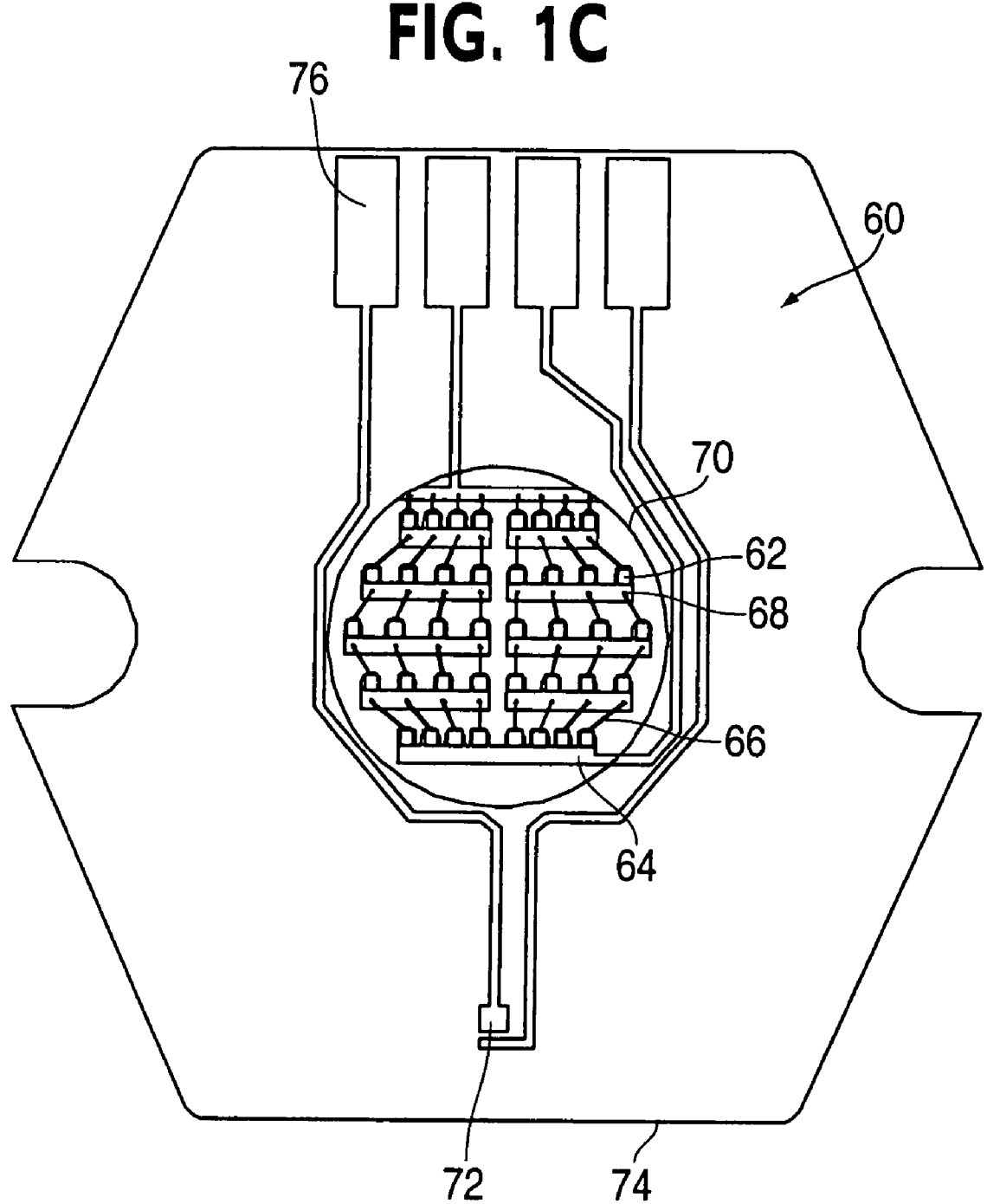

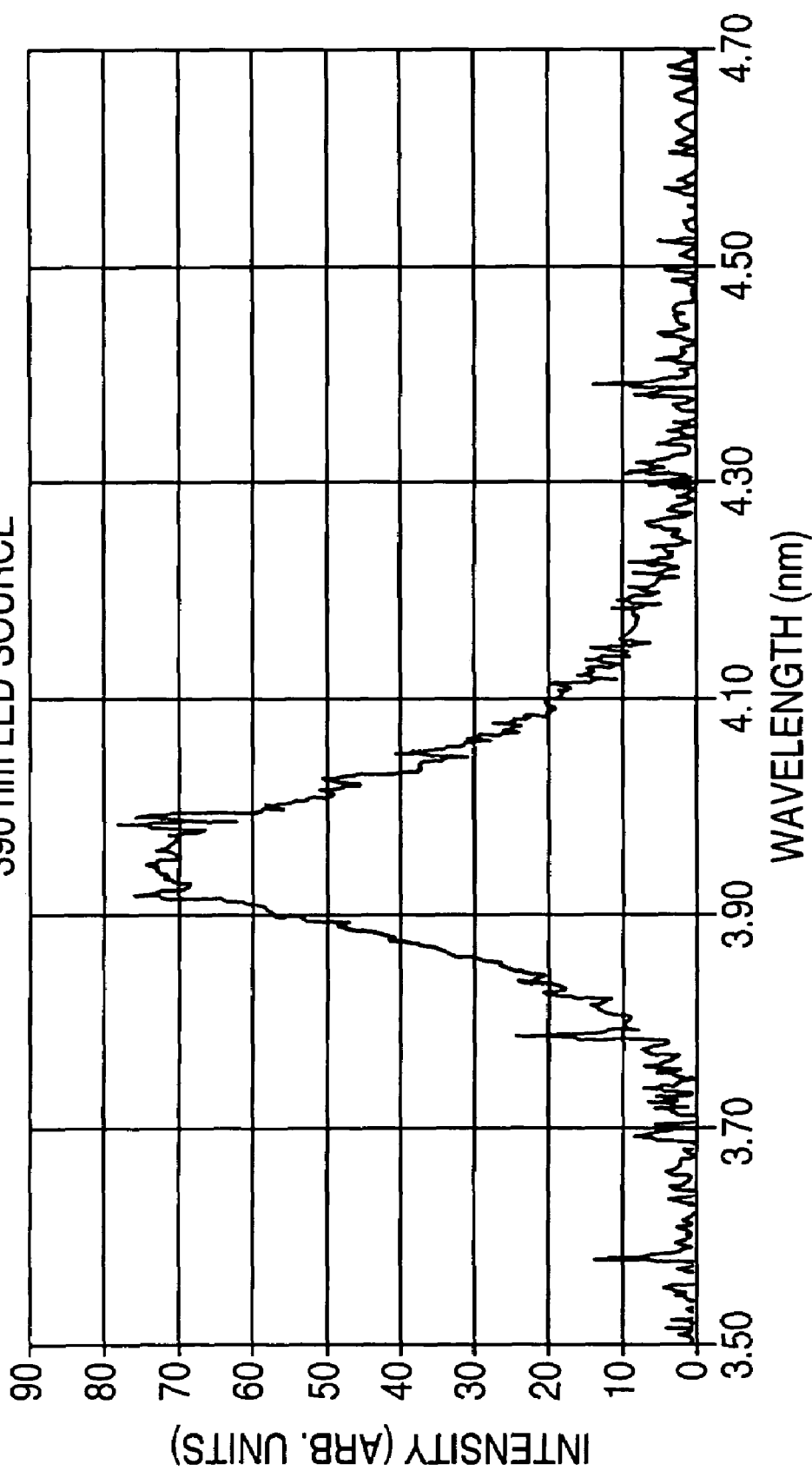

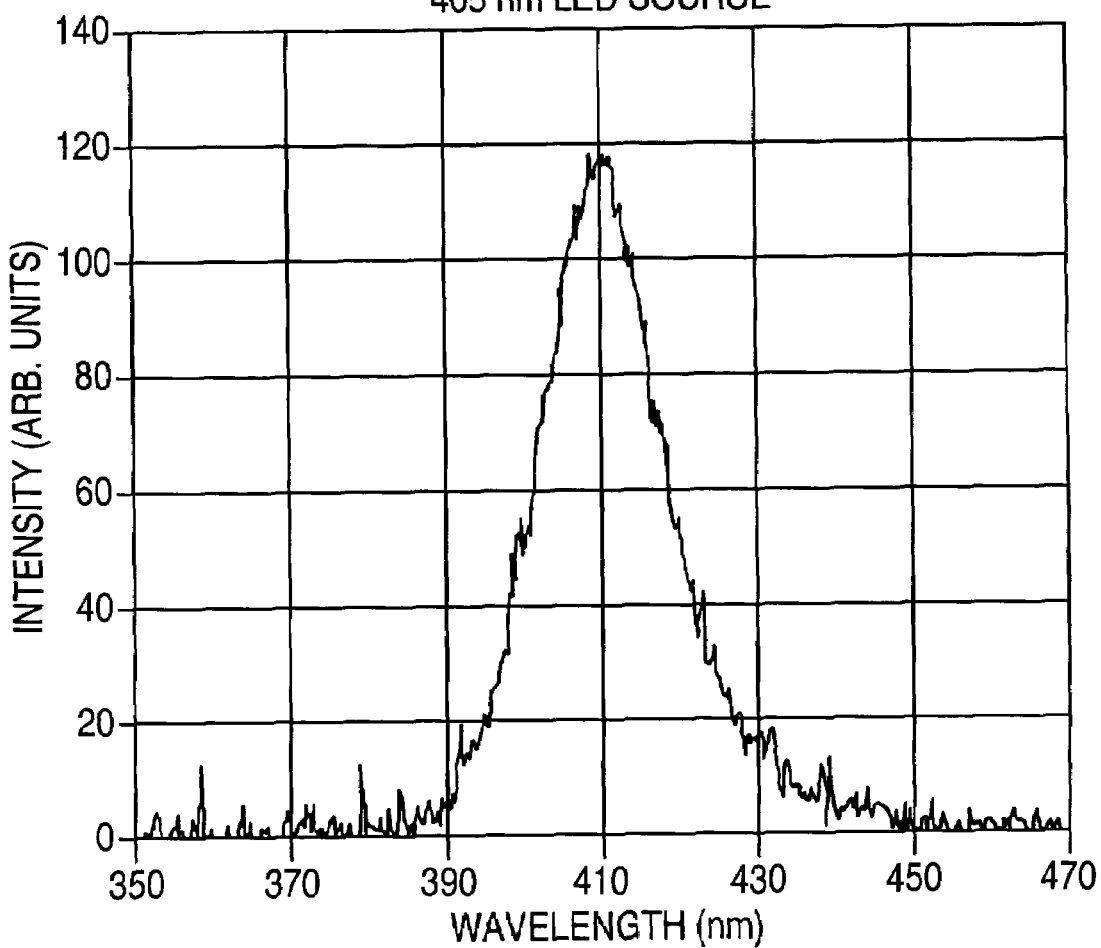

SOLID-STATE LIGHT SOURCES FOR CURING AND SURFACE MODIFICATION

BACKGROUND OF THE INVENTION

1. Field of the Invention

The present invention pertains to an apparatus and method of providing substantially improved radiation beams for the treatment of surfaces, thin films, coatings, fluids or objects. More particularly, the present invention pertains to an apparatus and method for optically combining the light output of at least two arrays of solid-state light emitters to produce a light beam that has a selected spectrum chosen for applications requiring a wide range of wavelengths to improve or accelerate a treatment process with a controllable irradiance.

2. Description of the Prior Art

Radiant energy is used in a variety of manufacturing processes to treat surfaces, films, coatings, over layers, and bulk materials. Specific processes include but are not limited to curing, fixing, polymerization, oxidation, purification, or disinfections. By way of example, the manufacture of components for motor vehicles involves the application of under coatings, paints or clear coatings on vehicle surfaces for various purposes including corrosion resistance, decoration or surface protection (e.g. scratch resistance). The coatings or paints are resins or polymer-based materials that are applied as liquids or powders and require thermal or radiant energy processing to become solids. The processing of coatings or paints by thermal methods is slow and requires times ranging from minutes to hours to complete. In addition, some materials (for example, substrates or coating components) may be heat sensitive and damaged by thermal treatments.

Non-thermal curing using radiant energy to polymerize or effect a desired chemical change is rapid in comparison to thermal treatment. Radiation curing can also be localized in the sense that curing can preferentially take place where the radiation is applied. Curing can also be localized within the coating or thin film to interfacial regions or in the bulk of the coating or thin film. Control of the curing process is achieved through selection of the radiation source type, physical properties (for example, spectral characteristics), temporal variation, or the curing chemistry (for example, coating composition).

A variety of radiation sources are used for curing, fixing, polymerization, oxidation, purification, or disinfections of a variety of targets. Examples of such sources include but are not limited to photon, electron or ion beam sources. Typical photon beam sources include but are not limited to arc lamps, incandescent lamps, electrodeless lamps and a variety of electronic (that is lasers) and solid-state sources (that is solid state lasers, light-emitting diodes and diode lasers). Selection of a specific radiation source for an application is contingent on the requirements of the treatment process and the characteristics of the radiation source. These characteristics are related to but are not limited to the physical properties of the source, its efficiency, economics, or characteristics of the treatment process or target. For example, arc lamps or radio-frequency or microwave driven "electrodeless" ultra-violet sources efficiently produce high levels of radiated power having applications in many "industrial" processes where rapid treatment using significant levels of irradiance or energy density over large areas are needed. Arc or electrodeless lamps require high voltage, microwave or radio frequency power supplies and in the case of microwave-driven systems, a microwave tube (that is a magnetron). These high-powered lamps also require cooling and heat rejection systems. Such operational requirements limit the application of such photon sources to situations were this need can be met.

The spectral emissions of arc and electrodeless lamps are controlled by the conditions under which the lamp is operated, the particular gases used to fill the bulb and the selection of various additives placed in the bulb. Those skilled-in-the-art formulate specific lamp fills meeting curing needs for many photochemical processes, but gaps exist in spectral coverage in certain spectral ranges.

Solid-state light sources, such as, but not limited to, light emitting diodes (LEDs), diode lasers, diode pumped lasers and flash lamp-pumped solid-state lasers provide emission sources that can tuned to the needed wavelength or can be combined as arrays to provide a multi-wavelength source for applications needing broadband source. Advances in solid-state source technology provide high-brightness ultraviolet LEDs suitable as sources for radiation treatment.

At the present time, commercial UV emitting diodes emitting radiation down to an output of 370 nm. are available from Nichia, Cree, Agilent, Toyoda Gosei, Toshiba, Lumileds and Uniroyal Optoelectronics (Norlux).

UV emitting LEDs and laser diodes are constructed using large band gap host materials. InGaN based materials can be used in LEDs emitting at peak wavelengths ranging from 370 to 520 nm (for example, from the ultra-violet (UV-A) to visible green). The band gap of GaN is 3.39 eV and can accommodate luminescent transitions as large as 363 nm. The substitution of In into the GaN host provides localized states that can radiate in the ultraviolet down to 370 nm.

Other nitride materials such as InAlGaN can emit ultraviolet radiation in wavelengths as short as 315 nm. InAlGaN is already being used to make high brightness LEDs and laser diodes that operate in the range of 315 to 370 nm. Hirayama et al (Appl. Phys. Lett. 80,207 (2002)) reports devices employing layered structures of $In_xGa_{1-x}N$ or quaternary $In_xAl_yGa_{1-x-y}N$ grown on $Al_xGa_{1-x}N$ (x=0.12-0.4) have been used in multiple quantum well structures to produce sources emitting comparable flux at 330 nm to InGaN devices operating at 415-430 nm. Hirayama et al. (Hirayama et al, Appl. Phys. Lett, 80, 1589 (2002)) has also reported a room temperature LED source using an improved multiple quantum well (MQW) structure and InAlGaN materials which emits intense UV radiation at 320 nm and significant emission at 300 nm.

Hirayama et al. (Appl. Phys. Lett. 80, 37 (2002)) report that $Al_xGa_{1-x}N(AlN)/Al_yGa_{1-y}N$ MQWs exhibit efficient photoluminescence between 230 to 280 nm and that the photoluminescence is as high as that of the InGaN-based materials used in the violet diodes now commercially available. AlN-based materials are likely candidates for making ultraviolet LEDs operating in the UV-B or UV-C ranges. Other researchers are studying carbide and diamond materials as hosts for deep-UV based on the fact that their band gaps are as large as AlN.

LEDs operating in the blue, violet and UV-A (390 nm) wavelengths are of sufficient radiance to be used in ultraviolet and photochemical curing as "spot" curing sources. U.S. Pat. No. 6,331,111B1 (Cao) and EP 0-780-104 (Breuer et al) describe hand held portable spot curing light systems using solid state light sources consisting of light emitting diodes or diode laser chips. The light source of Cao may contain sources that emit multiple wavelengths so that numerous components in materials whose photo initiators are sensitive to different wavelengths may be cured at once. In the preferred embodiment described in Cao, the light travels directly to the curing surface without going through an optical device like a light guide or optical fiber. Breuer et al. describe a similar device optimized to cure dental resins and also extend claims to apparatus where the irradiator is a stationary curing apparatus whose light source chips are fixed to the walls of the curing chamber.

Various light sources have been used for the purposes of curing composite materials. These include plasma, halogen, fluorescent, and arc lamps. Various lasers have been incorporated in curing apparatus. Lasers emitting ultraviolet beams include frequency doubled or re-doubled sources like the 266 nm Nd—YAG systems, argon-ion systems and Nd—YAG pumped OPOs (optical parametric oscillators). Cao cites U.S. Pat. Nos. 5,420,768, 5,395,769, 5,890,794 and 5,161,879 where LEDs have been employed as curing light sources. The application of solid state sources to the curing process are also described in U.S. Pat. Nos. 6,127,447 and 5,169,675.

Technology necessary for the application of solid-state sources in the treatment process can be found in the development of LED and laser diode equipped systems for illumination and solid-state displays. These systems include an apparatus for LED illumination that can be incorporated into a hand-held lamp, are battery powered and equipped with electronics that provide pulsed power to control lamp radiance and compensate for the decrease in battery voltage during battery discharge. Published U.S. Patent Application 2002/0017844 A1 teaches the use of optical systems to modify the field of view for LED emitters in displays where the field-of-view is restricted.

There are many examples in the prior art of the use of LEDs in arrays to synthesize multi wavelength emissions. U.S. Published Patent Application No. 2001/0032985 A1 teaches the installation of arrays of colored LEDs on a chip to make multicolored or white solid-state illumination sources. U.S. Pat. Nos. 6,016,038 and 6,150,774 disclose the method and electronics needed to generate complex, predesigned patterns of light in any environment. The use of computer controlled LED arrays to provide light sources capable of rapid changes in illumination and spectral selection are detailed in U.S. Pat. No. 6,211,626, which describes a system using sub-arrays of primary colored (red, green and blue) LEDs whose individual elements are addressable and which can be controlled by pulse modulation to emit varying amounts of light to synthesize a third color. U.S. Pat. No. 6,211,626 indicates that such computer-controlled arrays of light emitters are not new but that previous systems had limitations, which reduced the flexibility or efficiency of the illumination system. The use of computer control for lighting networks used in illumination is described in U.S. Pat. Nos. 5,420,482, 4,845,481 and 5,184,114.

U.S. Published Patent Application No 2002/0191394 teaches the use of a diffractive optical element (diffraction grating) for mixing light from monochromatic light sources like LEDs and making multicolor or white beams. The monochromatic light sources are positioned relative to the grating where light of that frequency is found in the diffracted order beams higher than the zeroth order. The mixed beam is the zeroth order beam. A white beam will be provided if sufficient frequencies are represented in the first and higher order beams being directed on the grating. Fraunhoffer diffraction is used to mix the monochromatic beams. This is different from the use of Fresnel Zone plates to accomplish the coupling of the multiple radiation sources

SUMMARY OF THE INVENTION

The present invention provides a solid-state light source and method which optically combines (mixes) the light output of at least two and preferably additional independently controllable discrete solid-state light emitter arrays to produce a light beam that has a selected multi-wavelength spectrum over a wide range of wavelengths such as from deep UV to near-IR to provide irradiance of a target surface with a controlled power level. Optical mixers combine light spectrums which are provided from the light emitter arrays to produce the controllable multi-wavelength spectrum.

Specific features of this light source permit changes in the spectral, spatial and temporal distribution of light for use in curing, surface modification and other applications.

This light source can be adjusted to precisely match the physical characteristics of the applied light to the chemical properties of materials to provide a means to improve the process at both nanometer and greater length scales by:

(1) optimizing the degree and rate of cross-linking of polymeric materials;
(2) selecting specific cross-link bonding in polymers;
(3) matching light source characteristics to specific photoinitiators;
(4) controlling the distribution, penetration or rate of light energy deposition in materials to create new morphologies; and
(5) optimizing light source characteristics for surface processing.

A preferred embodiment of the invention comprises at least two solid state light emitting arrays which preferably are LED arrays, each of which has a characteristic emitting frequency (wavelength), an optical mixer to mix the radiation from the LED arrays, a reflector to concentrate radiation from the arrays and to provide a two-dimensional energy distribution on the target surface to be treated which is optionally substantially uniform. An optional cooling system may be provided to provide high stability of the spectral output and to improve lifetime of arrays.

The invention increases the flexibility of the photochemical processes (especially, but not limited to, UV-curing of inks and the like, plastic, thermal paper, liquid crystal and the like) by either optimizing existing ultraviolet treatment processes and outcomes, or creating entirely new treatment processes or outcomes. The invention performs these tasks by providing a light source whose spectral emissions can be varied to provide changes in the ultraviolet light such as to changes in the brightness, chromaticity, calorimetric purity, hue, saturation and lightness of visible light. Modification of physical characteristics of light provides configuration of a light source to make the best use of the physical and chemical properties of curable materials.

Other problems which the invention overcomes include curing applications where the use of technology normally included in light sources cannot be used for technical, process or economic reasons. This includes but is not limited to:

(1) high voltage cabling, electronics and power supplies;
(2) RF or microwave cabling, wave guides, electronics and power supplies;
(3) gaseous electronic components including electrode and electrode-less bulbs
(4) high power electronics and the needed heat dissipation systems.

The invention also provides a solution to the problem of unwanted light emissions such as infrared from curing sources. Ultra-violet solid-state light emitter arrays generate little or no emissions in the infrared. If infrared radiation is needed in the curing process, infrared emitters of the desired wavelength and energy can be configured into the solid state UV generating arrays providing the selected wavelengths which are included in the curing light system to provide the desired missed spectrum.

The frequency spectrum of the individual light emitting arrays is chosen either (1) to provide a composite frequency made up of the mixed spectrum from the individual arrays required for the desired application, or (2) each array provides the identical common frequency spectrum to increase the power level of irradiance of the common frequency spectrum.

BRIEF DESCRIPTION OF THE DRAWINGS

FIG. 1C is an example of a light emitting array which may be used with the practice of the various embodiments of the invention.

FIG. 2 is the spectral distribution of irradiance of one of the LED arrays in FIG. 1 showing ultraviolet radiation source emission near 390 nanometers.

FIG. 3 is a spectral distribution of irradiance of the other LED array in FIG. 1 showing an ultraviolet radiation emission near 410 nanometers.

Like reference numerals identify like parts throughout the drawings.

DESCRIPTION OF THE PREFERRED EMBODIMENTS

The present invention is a solid state light source and a method of irradiating a target surface with a solid state light source which utilizes solid state light emitting arrays each preferably comprising a plurality of light emitting diodes (LEDs) which are mounted on a flat surface. Each diode emits light away from one side of the flat surface toward a target surface with at least one wavelength which is chosen to satisfy the desired application. At least one optical mixer is provided with each mixer mixing the output of a pair of solid state light emitting arrays. Each optical mixer is positioned symmetrically with respect to a pair of light emitting solid state arrays. Each optical mixer reflects part of the light output from a symmetrically disposed diode array and transmits part of the light output from another symmetrically disposed light array to provide a composite mixed light spectrum to irradiate the target surface with mixed light which has a selected frequency spectrum with the irradiance level of the spectrum being controllable by a variable control parameter such as voltage, but it should be understood that the invention is not limited thereto. The at least one optical mixer may be designed to substantially split (50-50) the light incident thereon from each array into a part which is reflected and a part which is transmitted through the optical mixer. With respect to the portion of the light which is transmitted through the optical mixer from the first light emitting array, the light incident on an opposite surface of the optical mixer from the other light emitting array which is reflected is optically mixed with the portion transmitted through the optical mixer from the first light emitting array. A composite wave front comprised of the mixed components of light from each of the symmetrically disposed solid state light emitting arrays is transmitted toward the irradiated target surface. As is described below, a controller controls the power applied to the light emitting arrays to control the irradiance which is incident on the target surface. Each light emitting array may have a substantially similar frequency spectrum or have a different frequency spectrum.

When the frequency spectrums of the symmetrically disposed light emitting arrays are different, the overall frequency of the irradiance on the target surface is a summation of the individual frequency spectrum output by the individual light emitting arrays. In each of the embodiments of the invention, mixing is produced by one or more optical mixers which may be a partially reflective and partially transmissive mirrors which may transmit and reflect substantially equal parts or transmit and reflect unequal parts or a prism which is irradiated by the light from the individual solid state light arrays to provide mixing thereof.

Figure 1A:
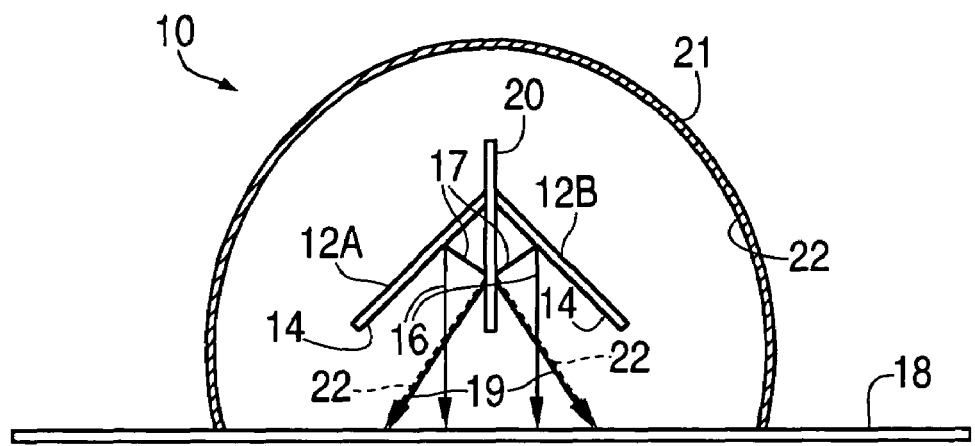
FIG. 1A is a side elevational view of a first embodiment of the present invention.
Figure 1B:
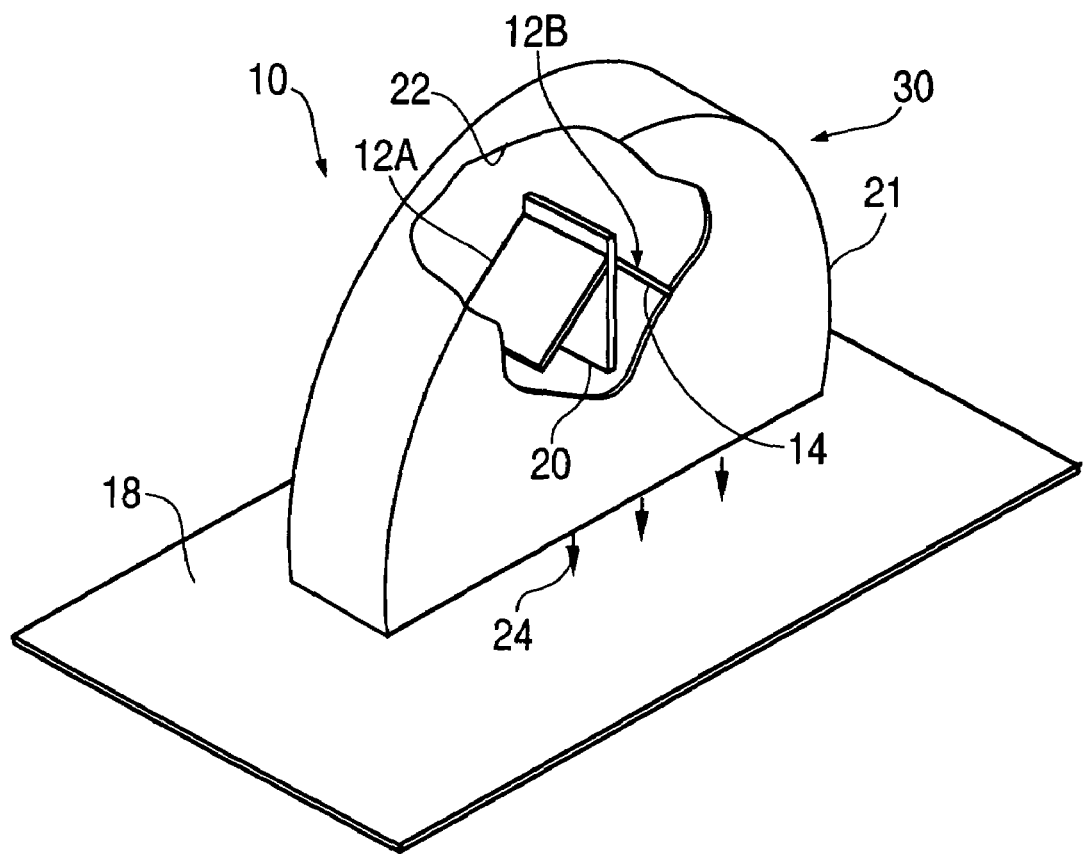
FIG. 1B is a perspective view of the first embodiment of the present invention.

FIGS. 1A and 1B illustrate a first embodiment 10 of the present invention. FIG. 1A is an elevational view with a section taken through a curved internally reflective housing 21; FIG. 1B is a perspective view of the embodiment 10; and FIG. 1C is an illustration of a suitable light emitting array which may be used with the practice of the invention.

The first embodiment 10 is illustrative of a basic solid state light source in accordance with the present invention. Each of light emitting arrays 12A and 12B may be manufactured in accordance with any well-known technique. The surface 14 of each of the pair of symmetrically disposed solid state light emitting arrays which, in a preferred embodiment, are LEDs output light rays 16 which pass directly to the target surface 18. Other light rays 17 produce a combined irradiance produced by optical mixing element 20 on which the rays 17 are incident thereon. As may be seen in FIG. 1A, the interior of housing 21 has an internally reflective surface 22 which functions to reflect any light output from either of the light emitting arrays 12A or 12B toward the target surface 18 to provide controlled irradiance which, in a preferred embodiment, is preferably substantially uniform thereon as described below in conjunction with FIGS. 2-6 in view of the curvature of surface 22 being elliptical with the optical mixer being near the focal axis of the elliptical curvature. Light rays 16, 17 and 19, which are output from the light emitting arrays 12A and 12B and do not pass through the optical mixer 20, are shown as solid lines and light rays 22 passing through the optical mixer 20, from either of the light emitting arrays 12A or 12B are shown as dotted rays. Parallel solid line rays 19 and dotted rays 22 symbolize the net mixing performed by the optical mixer 20 for the rays emitted from the surfaces of the light emitting arrays 12A and 12B which partially transmits and partially reflects the light emitted from the pair of light emitting arrays. The degree of reflection and transmission may be varied from an equal splitting.

The housing 21, while preferably having an elliptical cross section, may utilize other curved cross sections which facilitates converging divergent light rays produced by the solid state light arrays 12A and 12B being directed toward the target surface 18 as indicated by arrows 24.

The pair of light emitting arrays 12A and 12B are illustrated as square flat panels. The light emitting arrays are comprised of a plurality of devices, such as LEDs, which emit radiation in the ultraviolet range but the invention is not limited thereto with a suitable construction being described below in conjunction with FIG. 1C. For example, in a high power irradiation apparatus in accordance with the embodiment 10 of FIGS. 1A and 1B, the arrays 12A and 12B may respectively be an array of 40 LEDs as described in FIG. 1C which individually emit at 400 mW at 405 nm mounted on an integrated circuit of approximately 1 square cm. The other radiation source 12B may, without limitation, be an array of 40 LEDs as described below emitting 100 mW at 390 nm mounted on an integrated circuit of approximately 1 square cm. Additionally, the optical mixing element 20 may be semi-reflective mirror which substantially equally splits the emission from the rays 16 into reflected rays 19 and transmitted rays 22 which are mixed as indicated by the aforementioned parallel solid and dotted lines 19 and 22 such that the rays are superimposed onto each other. A semi-reflective mirror, which may be utilized as the optical mixer 20, may be a UV transmitting quartz plate that is coated with a thin chromium film that reflects and transmits approximately 50% of the incident light. The light emitting diode arrays 12A and 12B are symmetrically positioned with respect to the optical mixer 20 such that virtual images of radiation sources are superimposed to create in a preferred embodiment a mixed light source comprising substantially equal amounts of light from each of the light emitting arrays.

FIG. 1C illustrates a suitable construction for the light emitting solid state arrays 12A and 12B with a scale of approximately 5:1 for the first embodiment as described above and in the embodiments as described below. The array 60 is comprised of 40 LEDs 62. A lower bus bar 64 has a group of 8 LEDs mounted thereon. Each of the LEDs 62 mounted on the lower bus bar 64 are in turn coupled by a wire 66 by means of wire bonds 68 which connect the wire extending from the individual LEDs to four upper bus bars 64 on which 4 LEDs are mounted. A lens 70 focuses light emitted by the individual LEDs 62 toward the optical mixer 20. A thermal sensor 72 is utilized to provide temperature control for the LED array 60. The LED array 60 is mounted on a hexagonal substrate 74. Electrical terminals 76 are mounted on the hexagonal substrate 74 to provide suitable electrical contacts for electrical power of the array.

The light source represented by the light emitting solid state arrays 12A and 12B and the optical mixer 20 is positioned approximately at the focus of the elliptical reflector 22 which is preferably substantially one-half of an ellipse. However, the reflector 22 may be more or less than one-half of an ellipse if desired and may be a non-elliptical surface. Since the reflector 22 is part of an ellipse, the reflector 22 has a major axis, a minor axis, a first focal axis within the reflector, and a second focal axis outside the reflector. The light source comprised of the aforementioned light emitting and optical mixer is preferably positioned on the first focal axis. Light beams from the arrays of diodes 12A and 12B are transmitted and reflected by the optical mixer 20 and strike the elliptical reflector 22 that directs the light beams to the second focal axis of the elliptical reflector 22 proximate to the target surface 18. The target surface 18 is placed substantially at the second focal axis where the light beams are directed to strike the irradiated surface thereof. The location of the target surface 18 at the second focal axis maximizes the irradiance at the second focal axis. The irradiated surface 60 can also be placed beyond the second focal axis such as at the far field to increase the area which is irradiated.

FIGS. 2-6 illustrate the optical performance of the radiation on the target surface 18 using the first embodiment 10. The spectral readings were obtained using an integrated sphere and a spectral radiometer (Ocean Optics model S2000) based on techniques well-known in the field of illumination. The radiation sources were 40 light emitting diodes which are high flux density solid state modules manufactured by Norlux Monochromatic Hex (NHX) emitting either ultraviolet UV-A at a peak emission at 390 nm or ultraviolet UV-B at 405 nm with a peak emission at 410 nm. The LED arrays 12A and 12B were independently connected to DC power supplies operated at a constant voltage mode. A forward bias voltage turned the diodes on to produce the UV spectra of FIGS. 2-6.

FIGS. 2 and 3 show the spectral irradiance of the source 12A which is a UV-A emitter and the source 12B which is a UV-B emitter. Radiation source 12A was operated at forward bias of 15.6 volts and a current of 200 nA. Array 12A emitted UV-A ultra-violet radiation that peaked at 395 nm and extended from 385 to 405 nm (Full-Width-at-Half-Maximum) (FWHM). Diode array 12B was operated at a forward bias of 19 volts and a current of 200 mA to produce UV-B ultraviolet radiation that peaked at 410 nm and extended from 400 to 418 nm (FWHM).

Figure 4:
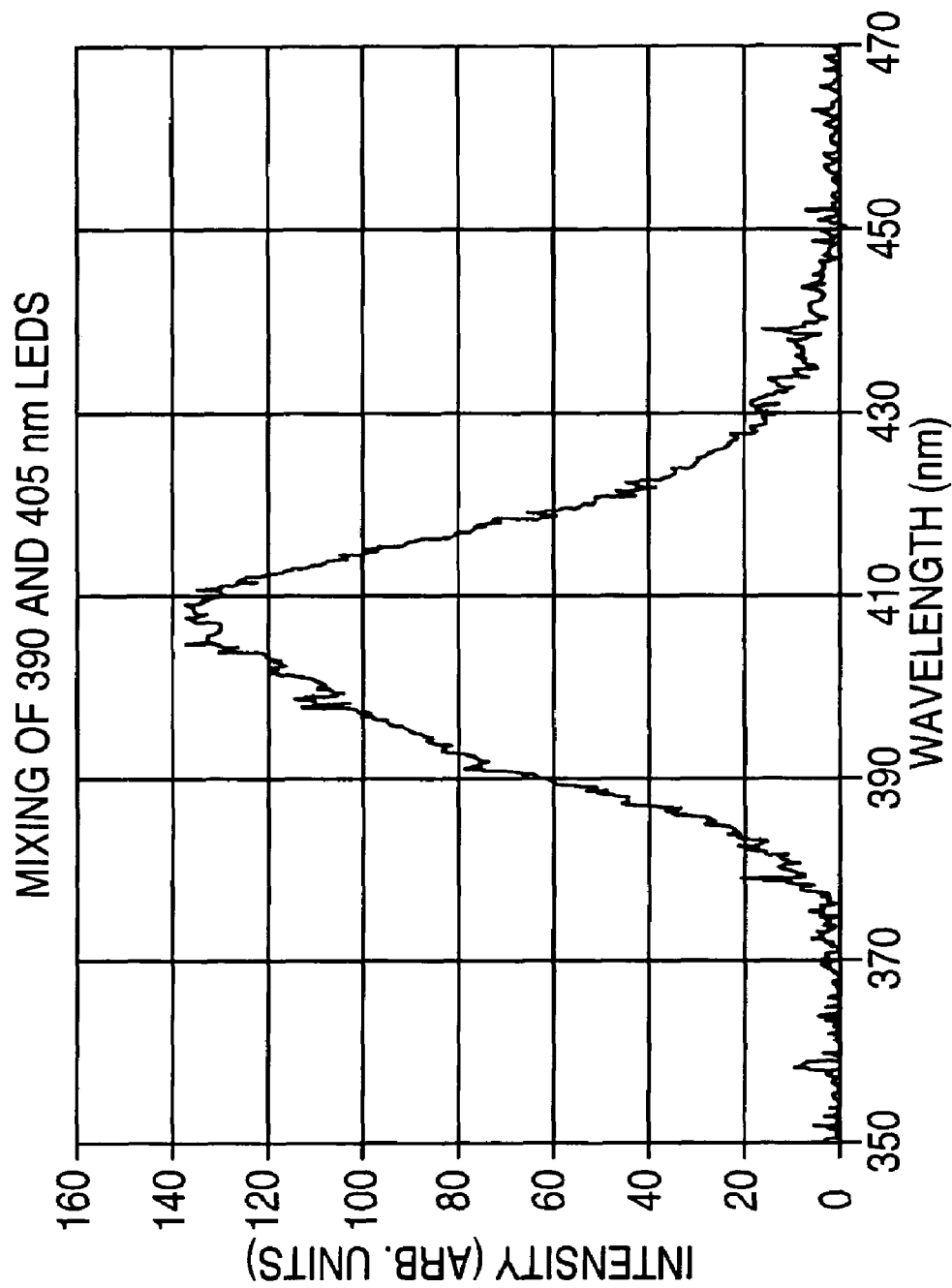
FIG. 4 is a spectral distribution of irradiance produced by optical mixing of the individual spectral radiance distribution of the LED arrays of the embodiment of FIG. 1 with the spectrums illustrated in FIGS. 2 and 3.

FIG. 4 shows a measured spectral radiance of embodiment 10 when both radiation sources 12A and 12B were operated simultaneously. The composite spectrum peaked at 410 nm and extends from 392 to 418 nm FWHM. The LED array 12A was operated at 15.6 volt forward bias, whereas the LED array 12B was operated at 17.5 volts forward bias. The spectrum is a composite of the summed emission from the two LED arrays 12A and 12B.

Figure 5:
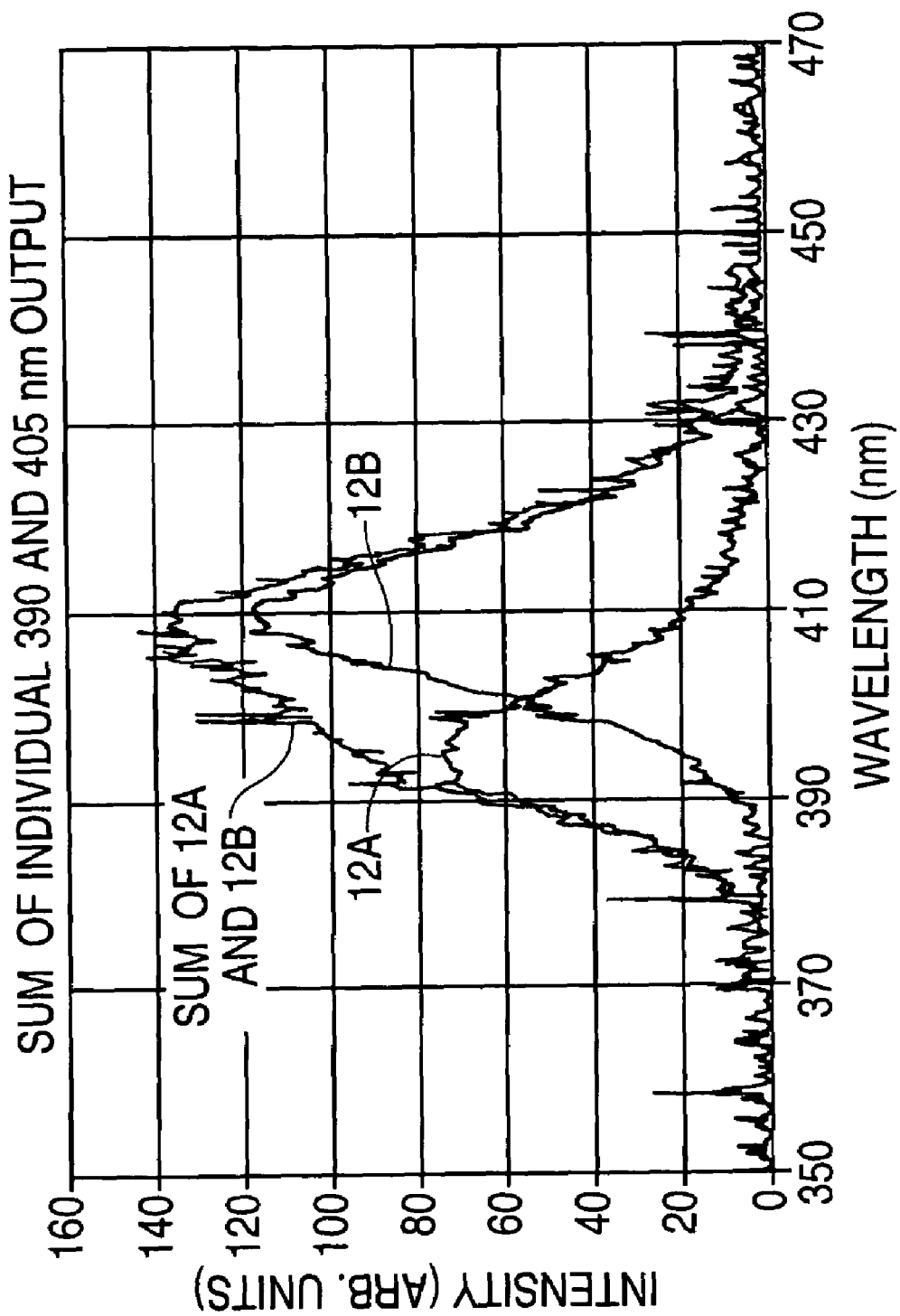
FIG. 5 is a spectral distribution of irradiance of the individual LED arrays showing the individual components of FIGS. 2 and 3 and the optical mixing thereof as illustrated in FIG. 4.

FIG. 5 illustrates the simulated spectrum produced by the summation of the individual emission spectra of the diode arrays 12A and 12B illustrated in FIGS. 2 and 3.

Figure 6:
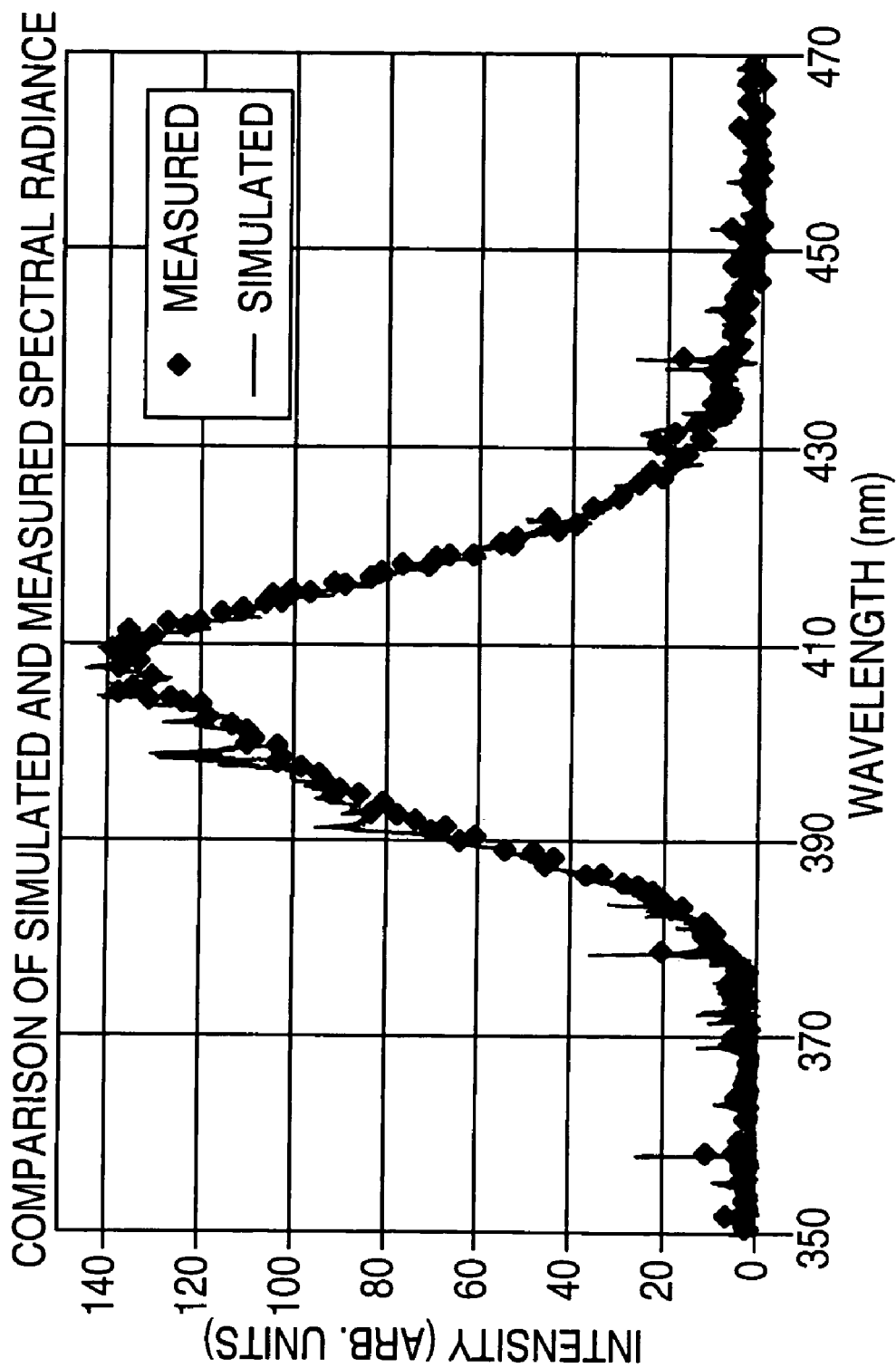
FIG. 6 is a comparison between measured and simulated spectral irradiance showing simulated spectral irradiance as a line and a measured spectral irradiance as diamonds regarding the embodiment of FIG. 1.

FIG. 6 is a comparison of the simulated and measured spectra of the embodiment 10. The measured spectra are identified by diamonds and simulated spectra are identified by lines. The measured spectrum matched a simulated spectrum over the entire range of emission from the light emitting arrays 12A and 12B and shows an excellent mixing of the beams from the two radiation sources.

The power levels of the light from the light emitting arrays 12A and 12B are controlled by varying the electrical bias applied thereto which changes the forward bias current of the diodes. The variation of voltage or another electrical parameter of the individual light emitting arrays 12A and 12B permits the variation of the spectral characteristic of the mixed light by choosing the magnitude and frequency of the spectra that are mixed by the optical mixer 20.

Figure 7:
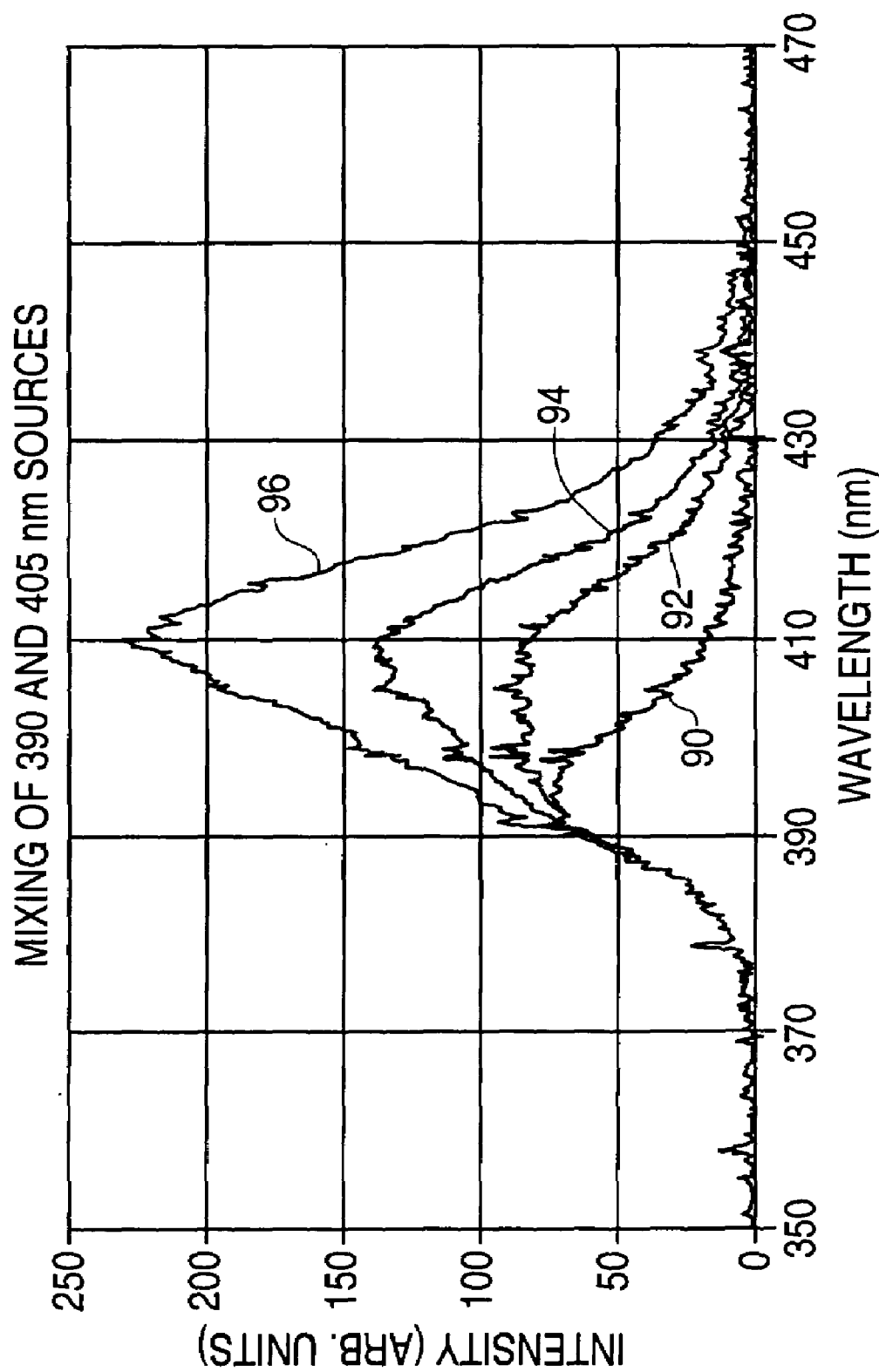
FIG. 7 is a spectral distribution of irradiance of the embodiment of FIG. 1 operated with the 390 nm LED array operated with a bias voltage of 47 volts and the 405 nm LED array operated at a bias voltage 0, 34, 35, and 38 volts respectively.

FIG. 7 shows how the spectral composition of a beam from the embodiment 10 can be changed continuously from (1) a spectrum 90 representing the wavelengths from the diode array 12A, (2) a spectrum 92 with equivalent contributions from the diode arrays 12A and 12B, (3) a spectrum 94 with an increased spectrum from the array 12B, and (4) finally to a spectrum 96 with the dominant contribution from the array 12B. This demonstrates an important function of the embodiments of the invention including the representation of the spectral composition of FIG. 1 which permits generation of a spectrum with variable ultraviolet spectral weight.

Figure 8:
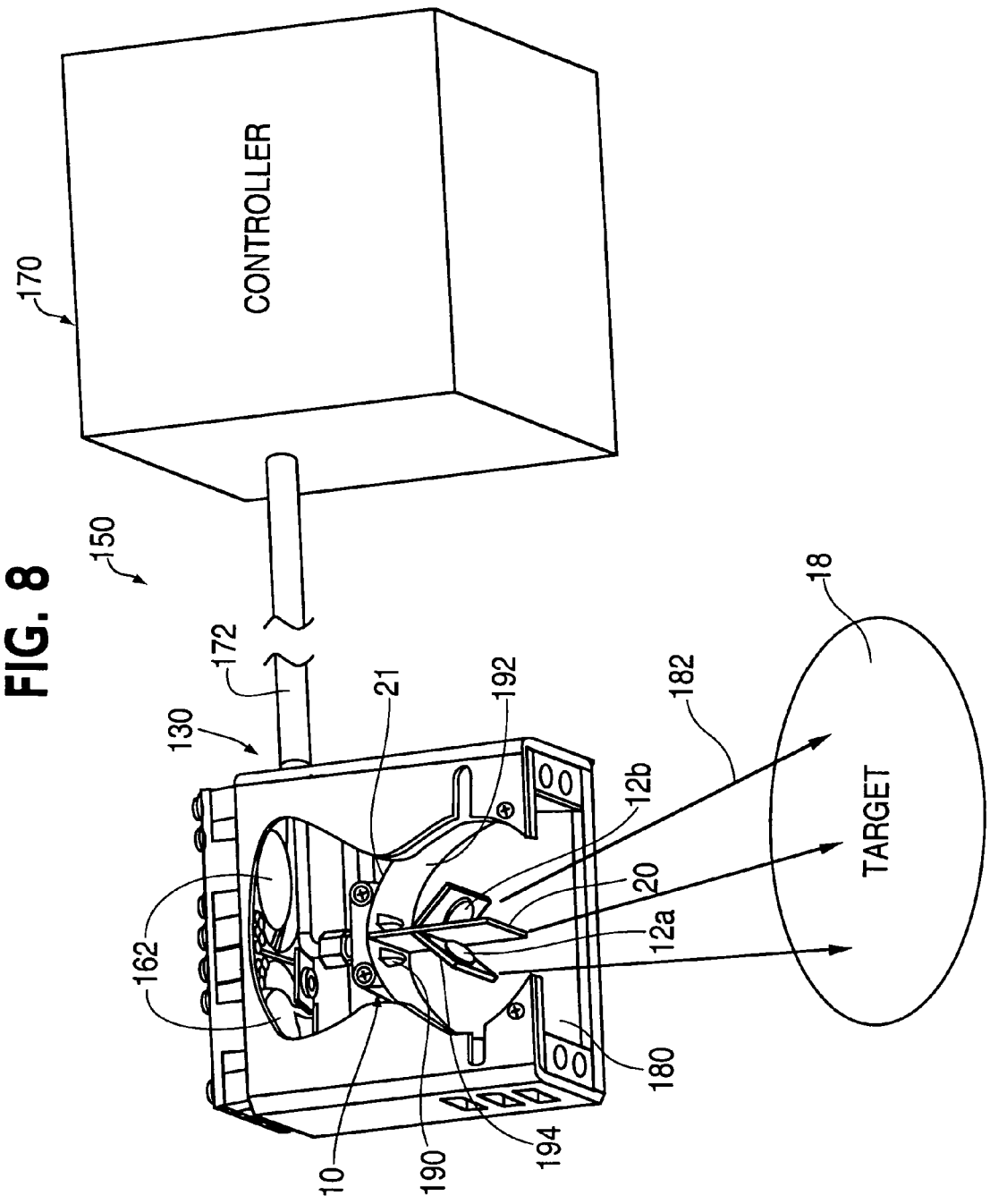
FIG. 8 shows an embodiment of the invention using two solid state light emitting arrays as illustrated in FIG. 1, including a housing with an interior elliptical reflector installed in a lamp enclosure providing cooling to the solid state light emitting arrays and a controller for controlling the power and spectral output produced by the individual solid state light emitting arrays.

FIG. 8 illustrates a system 120 incorporating the embodiment 10 of FIG. 1 into a lamp housing 130 which is equipped with a cooling system for the LED arrays 12A and 12B. The air cooling system may be by forced air utilizing one or more fans inducting air into the housing and blown past the interior curved reflector 21. As may be seen, pathways exist for the ingress and egress of cooling air. A controller 170 is coupled via connection 172 to the solid state light source. The curved reflector 21 is mounted in the lamp housing 130 with the reflector being attached to a base of the lamp enclosure that has a rectangular opening 180 from which light rays 182 pass to the target surface 18. The LED arrays 12A and 12B are air cooled by two fans 162 which push air into the lamp enclosure 130. A slot 190 is cut into the curved reflective surface 21 to permit air to be pushed into the lamp enclosure 192 to allow the air to impinge on heat sinks 194 of the LED arrays 12A and 12B which are attached thereto. The fans 162 may be powered from a 12 volt power supply. The LED arrays 12A and 12B will suffer a loss of light emitting power if a surface temperature of the substrate to which the LEDs 12A and 12B are attached exceeds 40° C. with current commercially available products. The power to the diode arrays 12A and 12B and the speed of the fans 162 is adjusted to keep the LED chip surfaces below the maximum temperature, such as 40° C. The controller 170 may be digitally controlled which permits programming of the voltage to be applied to each of the diode arrays 12A and 12B in order to produce a variation in the summed output radiation as reflected, for example by the curves 90-96 in FIG. 7 once the frequency spectra is determined by the choice of the individual solid state light emitting elements of the array.

Figure 9:
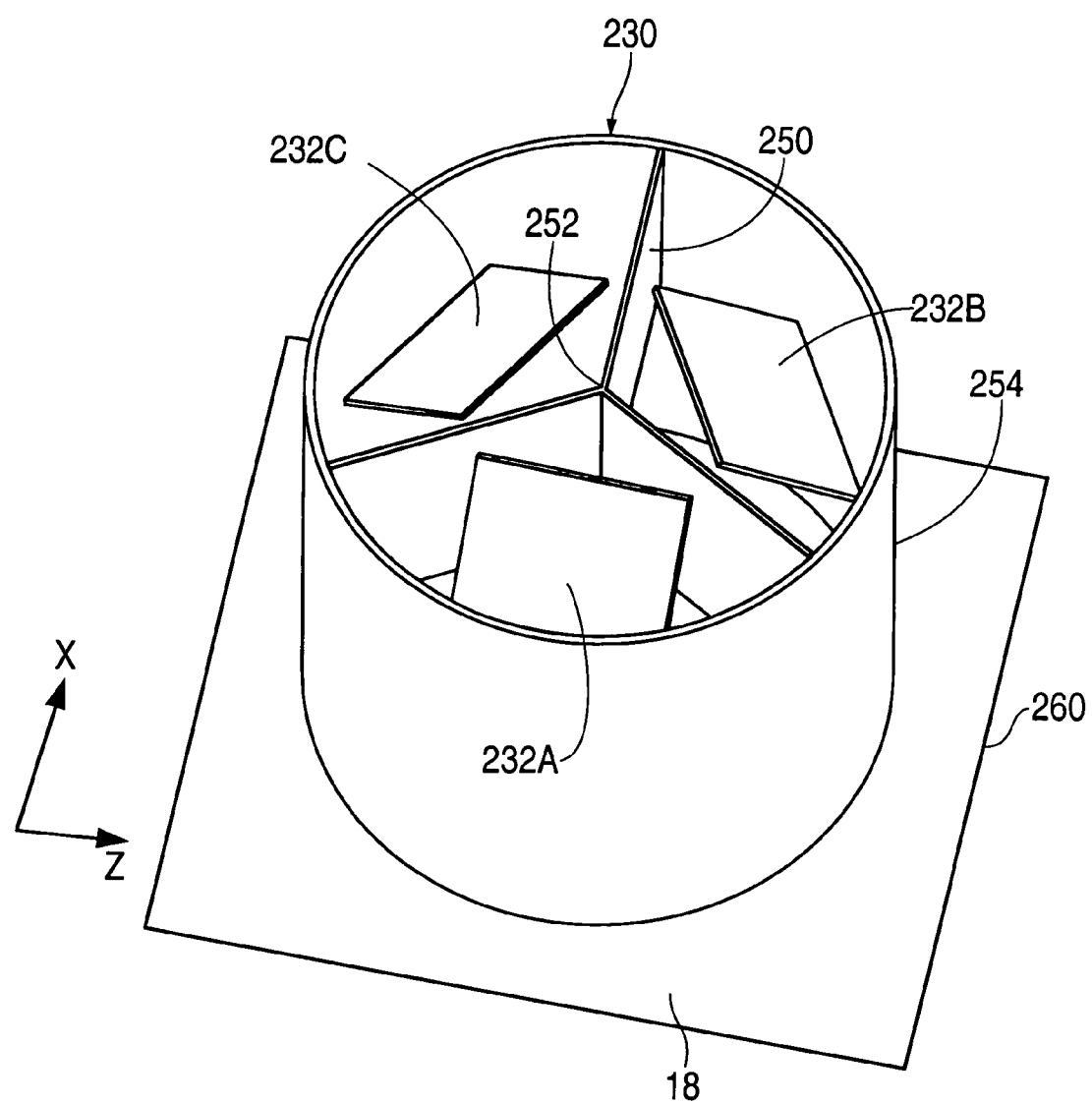
FIG. 9 is a perspective view of a second embodiment of the invention utilizing three solid state light emitting arrays, three semitransparent mirrors functioning as optical mixers and an interior cylindrical reflector.

FIG. 9 illustrates a third embodiment 230 of a solid state light source in accordance with the invention which is comprised of three LED arrays 232A, 232B and 232C and three optical mixers 250 which intersect at a central point 252 within cylindrical reflector 254. The three LED arrays 232A, 232B, and 232C produce spectra which are mixed by the symmetrically disposed optical mixer 250 located therebetween. The aforementioned LED arrays and symmetrically positioned optical mixtures 250 perform the same function as described above with respect to the first embodiment 10 of FIG. 1. The individual optical mixers 250 which intersect at central point 252 have an occluded angle of 120° between the adjacent optical mixers. The optical mixers 250 preferably are semi-reflective mirrors which split the emission substantially equally from the LED arrays 232A, 232B and 232C into three transmitted and reflected beams of substantially equal intensity which are superimposed onto each other as indicated in FIG. 1 by the superimposed light rays 19 and 22. However, this embodiment may use optical mixers which do not transmit and reflect equal parts. The three optical mixers 250 are symmetrical when rotated through an angle of 120°.

Figure 10A:
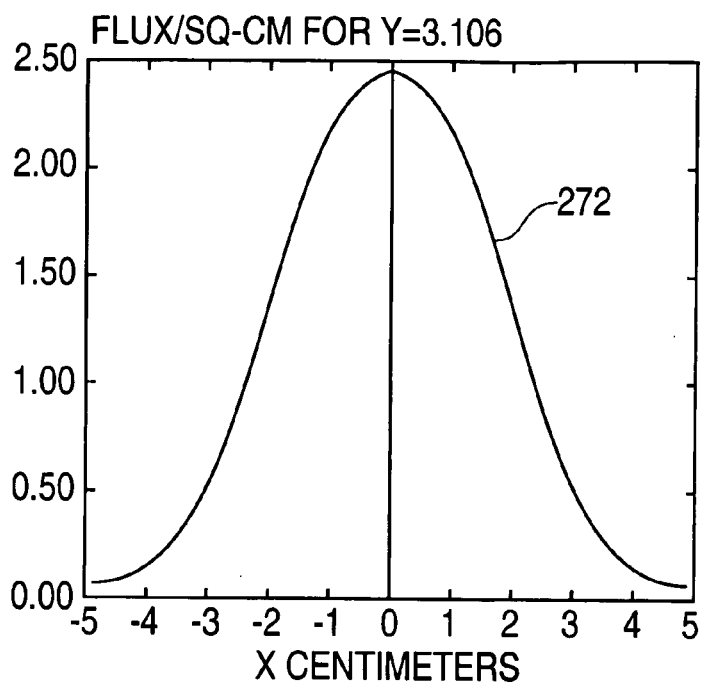
FIGS. 10A and 10B show a simulated flux distribution of the second embodiment of FIG. 9.
Figure 10B:
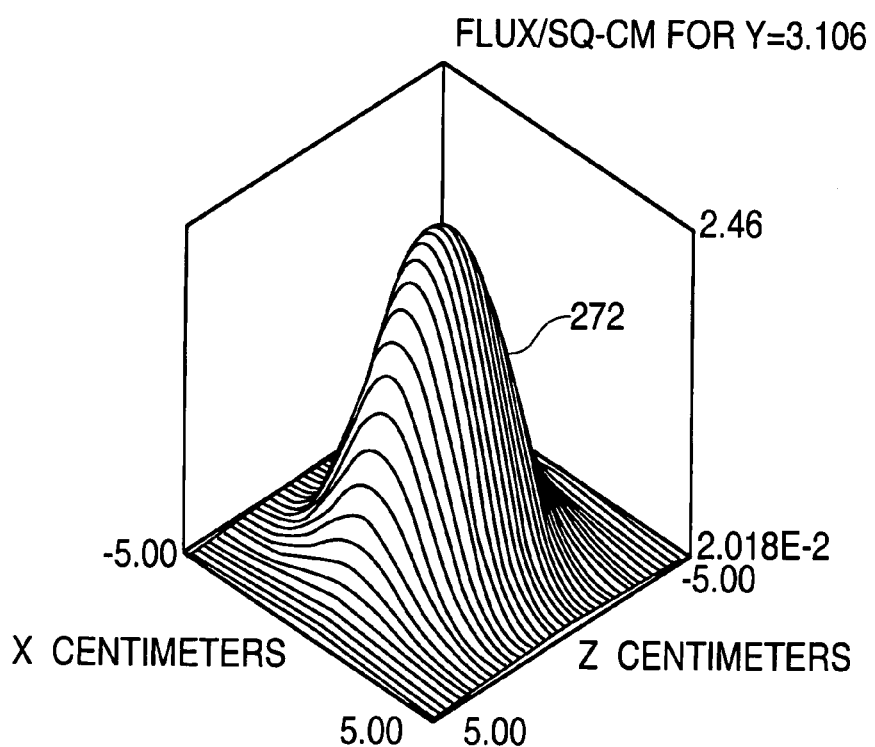

FIGS. 10A and 10B show the results of ray tracing simulations to predict the irradiance distribution 272 in the XZ plane as illustrated in FIGS. 10A and 10B for the second embodiment 230. The radiance profiles for traces parallel and perpendicular to the X or Z axis through the center of the irradiance distribution show small asymmetry 272. The asymmetry is a consequence of a lack of symmetry of the embodiment 230 to rotations 90° along an axis perpendicular to the XZ plane through the center of the embodiment 230.

Figure 11:
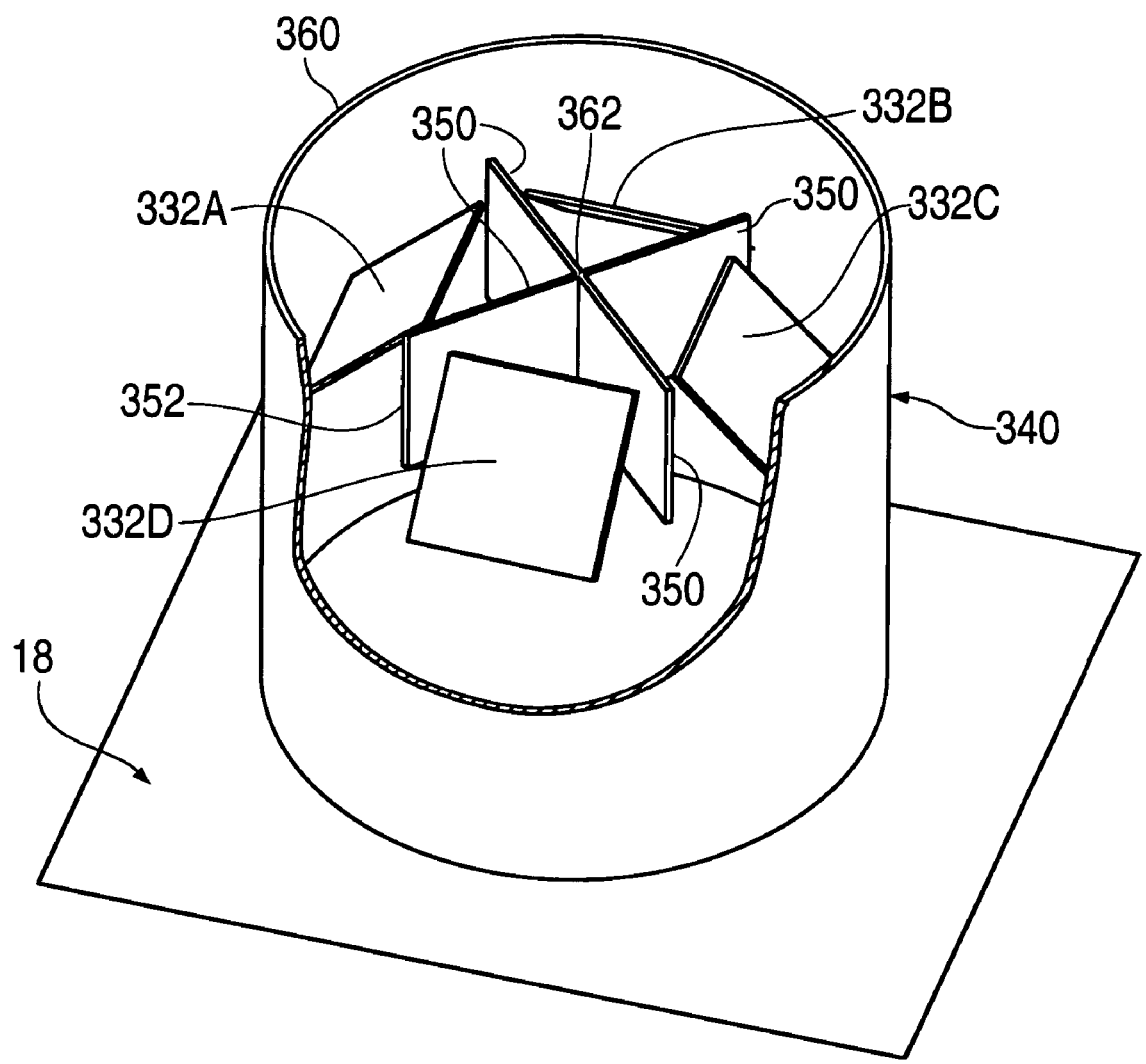
FIG. 11 illustrates a perspective view of a third embodiment of the invention in which four solid state light emitting arrays are placed between four semitransparent mirrors functioning as optical mixing elements and an interior cylindrical reflector.
Figure 12:
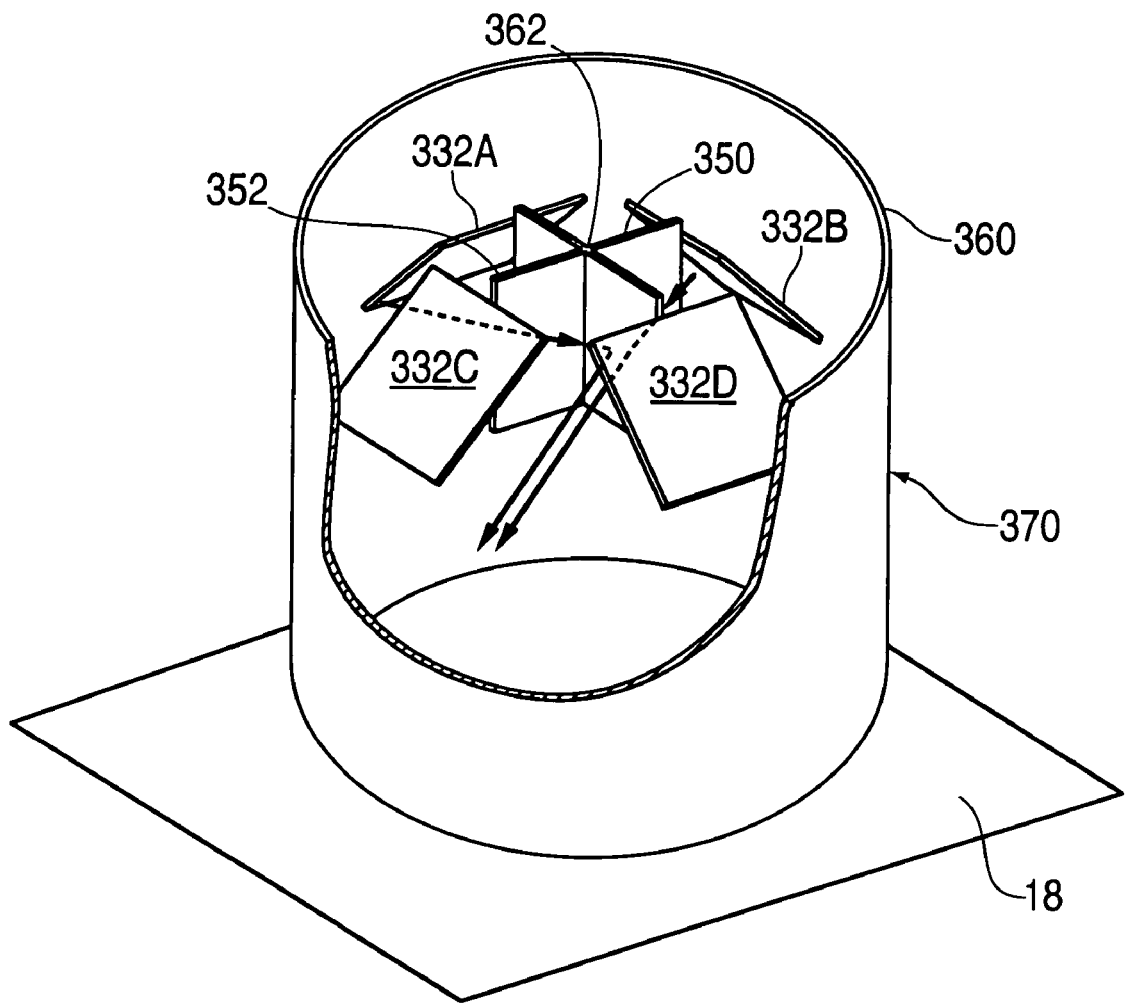
FIG. 12 is a perspective view of a fourth embodiment of the invention with four solid state light emitting arrays placed on the edges of four optical mixers and a cylindrical interior reflector.

FIGS. 11 and 12 respectively show a third and fourth embodiment 360 and 400. The designs respectively differ in the placement of the four LED arrays 232A-232D arrays relative to the intersection 362 of the placement of the optical mixers 350 so that the diode arrays 332A-332D are positioned between the edges 352 in FIG. 11 and face the edges 350 in FIG. 12. In the third embodiment 340, the LED arrays 332A-332D face the point of intersection 362 while in the fourth embodiment 370, the light emitting arrays 332A-332D face the edges 352 of the optical mixers 350. In the third and fourth embodiments, a cylindrical internally reflective housing 360 contains the LED arrays 332A-332D and the four optical mixers 350 centrally disposed relative thereto which are joined together at central location 362 to form a cross. In the fourth embodiment 370 a solid line indicates light rays which are visible to the viewer and a dotted line indicates rays which are occluded from direct view. It should be understood that the connections to a suitable controller and cooling system for the light emitting arrays, such as illustrated in FIG. 8, are not illustrated for purposes of simplifying the illustration.

Figure 13:
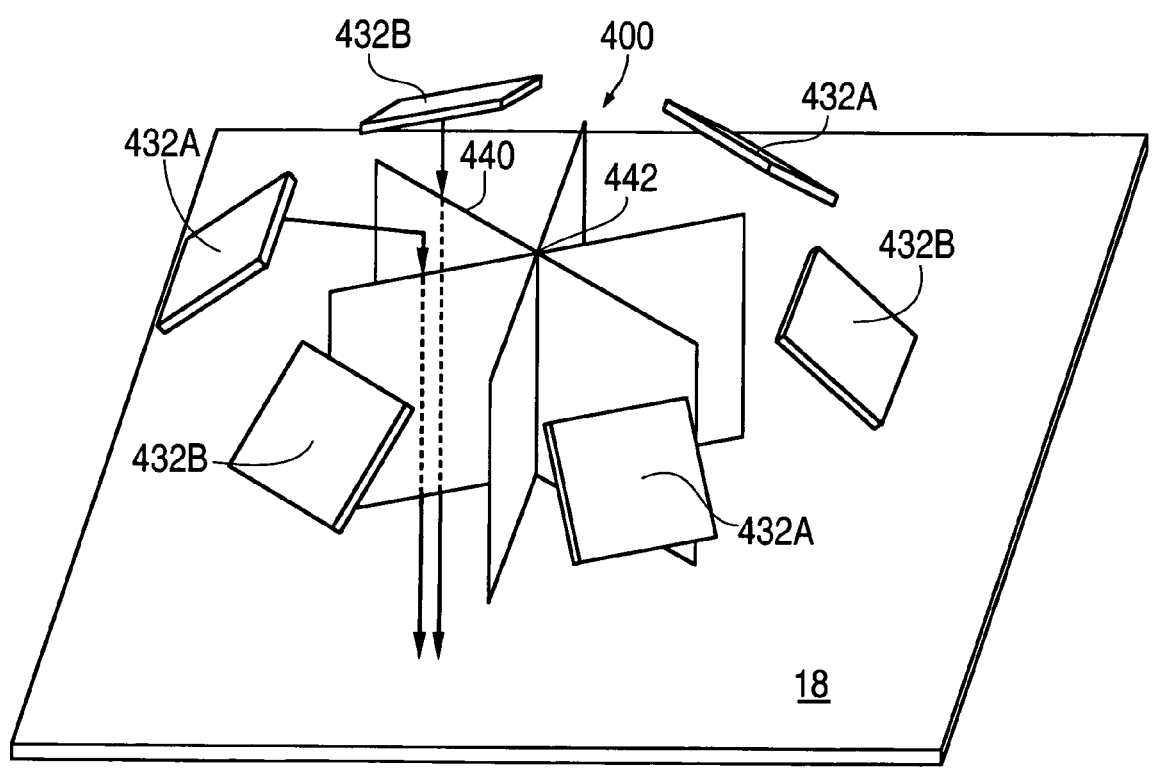
FIG. 13 is a perspective view of a fifth embodiment of the invention with six solid state light emitting arrays placed between six optical mixing elements.
Figure 14:
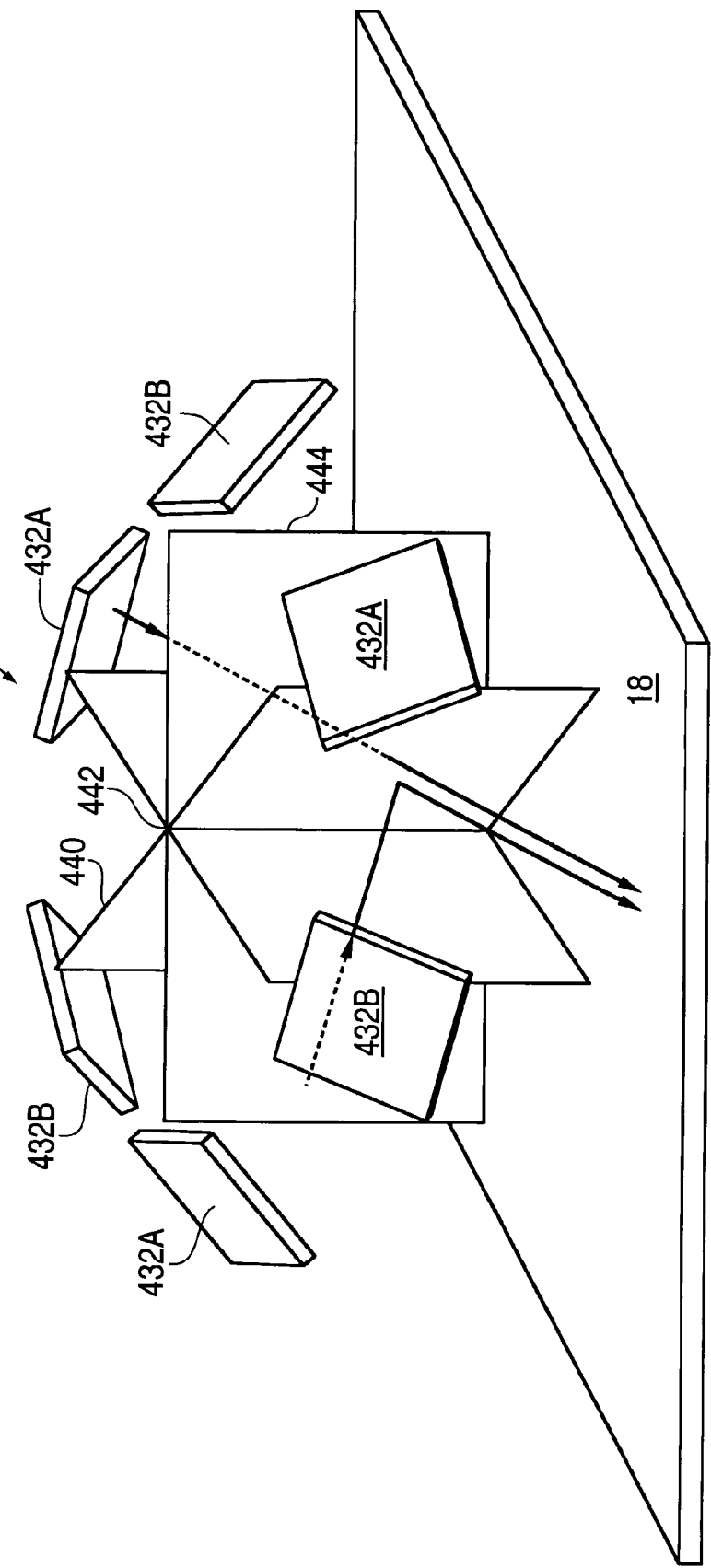
FIG. 14 is a perspective view of a sixth embodiment of the invention with six solid state light emitting arrays placed on edges of six optical mixing elements.

FIGS. 13 and 14 show fifth and sixth embodiments 400 and 420 respectively of the invention which have been simplified to only show the LED arrays emitted. The internally reflective curved housing has been omitted along with the controller of the individual LED arrays which is used to produce a controlled application of power to the individual LED arrays to produce a variable spectrum as discussed above. The embodiment 400 of FIG. 13 has three pairs of LED arrays 432A and 432B which are symmetrically disposed relative to optical mixers 440. Pairs of LED arrays 432A and 432B work in concert with their centrally disclosed optical mixer 440 to provide the same function as described above with respect to the first embodiment 10 to produce a controlled mixing of the light emitted from the surface of the pairs of the LED arrays. The difference between the embodiments 400 and 420 resides in the respective placement of the pairs of LED arrays 432A and 432B relative to the optical mixers 440. In the embodiment of 400, the pairs 432A and 432B face the point of intersection 442 of the optical mixers 440 and in the embodiment 420, the pairs 432A and 432B face the edges 444 of the optical mixers 440. The six optical mixers 440 are joined together at a central location 442 which is centrally disposed relative to the faces of the LED arrays 432A and 432B. The light from the three pairs of LED arrays 432A and 432B are combined by transmission and reflection of the six optical mixers 440 in accordance with the principal operation described above. While not illustrated, the embodiments 400 and 420 of FIGS. 13 and 14 may be placed inside of a cylindrical internally reflective housing of the type illustrated in FIGS. 1, 9, 10 and 11 so as to cause light to be transmitted toward a target surface 18. Additionally, a controller and a cooling system, such as that described above with respect to FIG. 8, may be utilized to control the emission of light from the LED arrays. The six optical mixers 440 in the embodiments 400 and 420 form a cross at a point of intersection 442 and preferably have the characteristic of reflecting and transmitting substantially equal intensity light. A solid line indicates light rays which are visible to the viewer and a dotted line indicates rays which are occluded from direct view.

Figure 15:
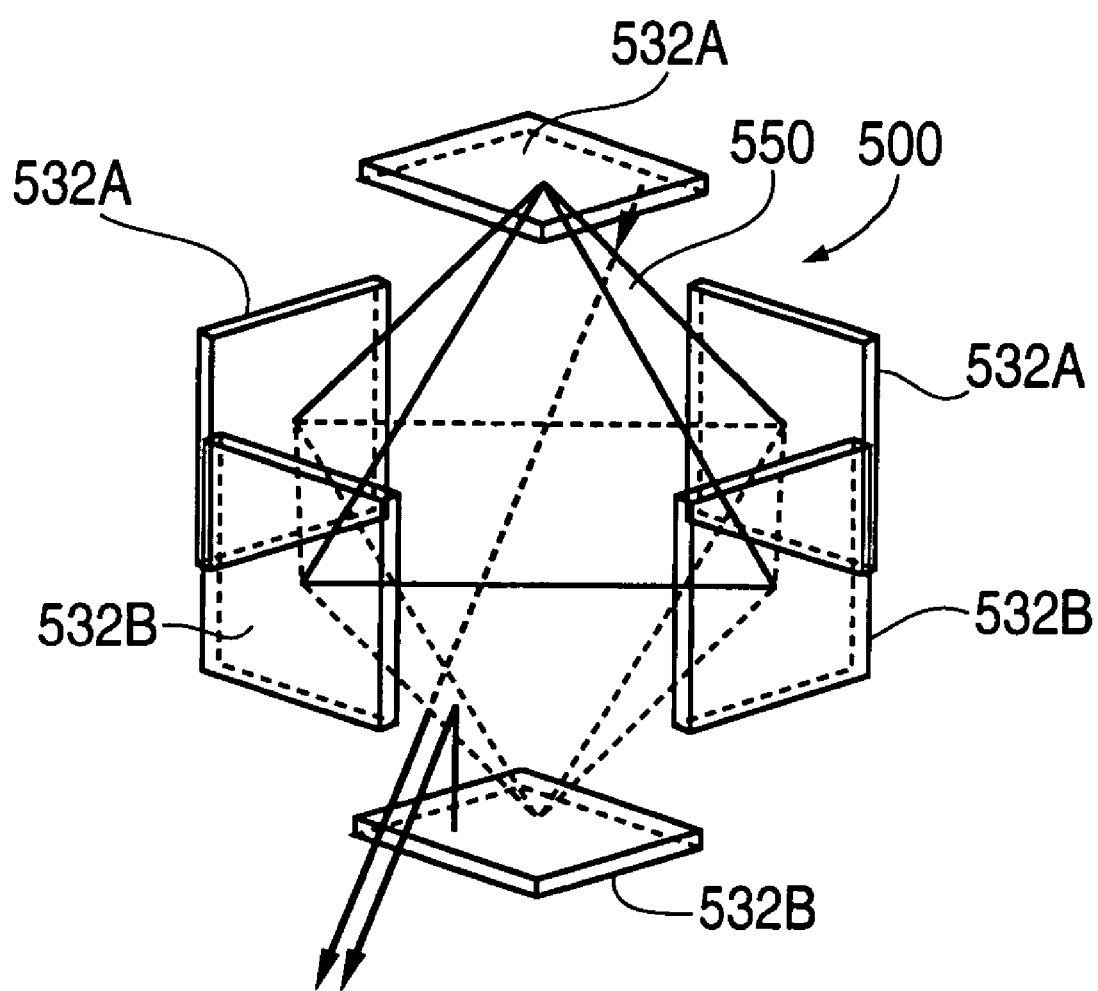
FIG. 15 is a perspective view of an seventh embodiment of the invention with six solid state light emitting arrays arranged facing eight optical mixers arranged in an octahedron.

FIG. 15 shows a seventh embodiment 500 having three pairs of light emitting diode arrays 532A and 532B which are symmetrically disposed about eight optical mixers 550 which are triangular semi-transparent mirrors which function to split the irradiation sources 532A and 532B into transmitted and reflected beams of substantially equal intensity which are superimposed onto each other in accordance with the mixing function as described above with respect to the first embodiment of FIG. 1. The LED arrays 532A and 532B are placed at the vertices placed at the edges of the optical mixers 550. It should be noted that the curved internally reflective housing, controller and target surface have been omitted from the embodiment of FIG. 15. A solid line indicates light rays which are visible to the viewer and a dotted line indicates rays which are occluded from direct view.

Figure 16:
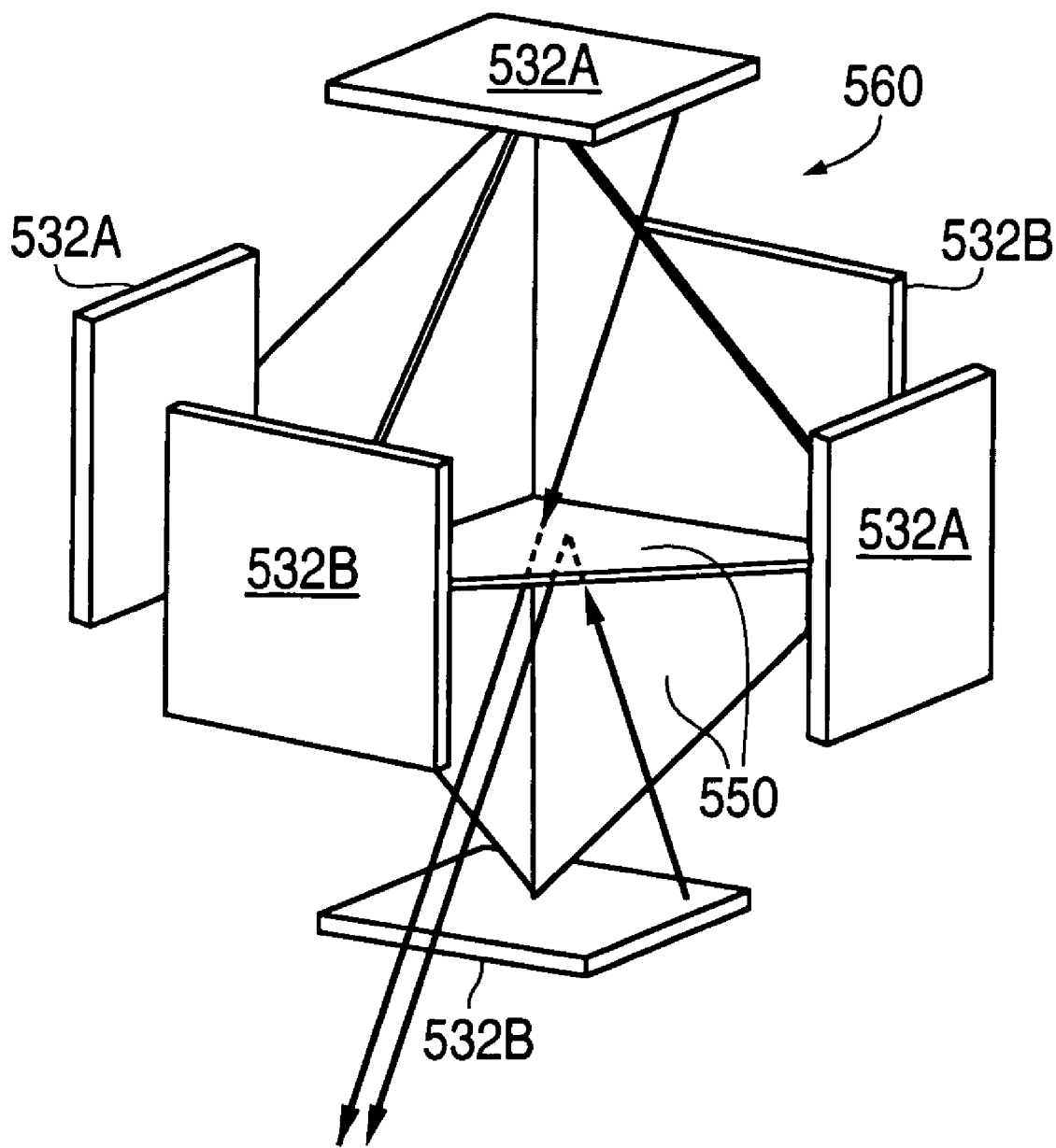
FIG. 16 is a perspective view of an eighth embodiment of the invention with six solid state light emitting arrays facing eight optical mixers.

The eighth embodiment 560 of FIG. 16 utilizes three pairs of LED arrays 532A and 532B which are positioned at the vertices of twelve optical mixers 550 which are partially reflective mirrors. Mixing of light from pairs of LED arrays 532A and 532B occurs in the manner described above. A solid line indicates light rays which are visible to the viewer and a dotted line indicates rays which are occluded from direct view.

Figure 17:
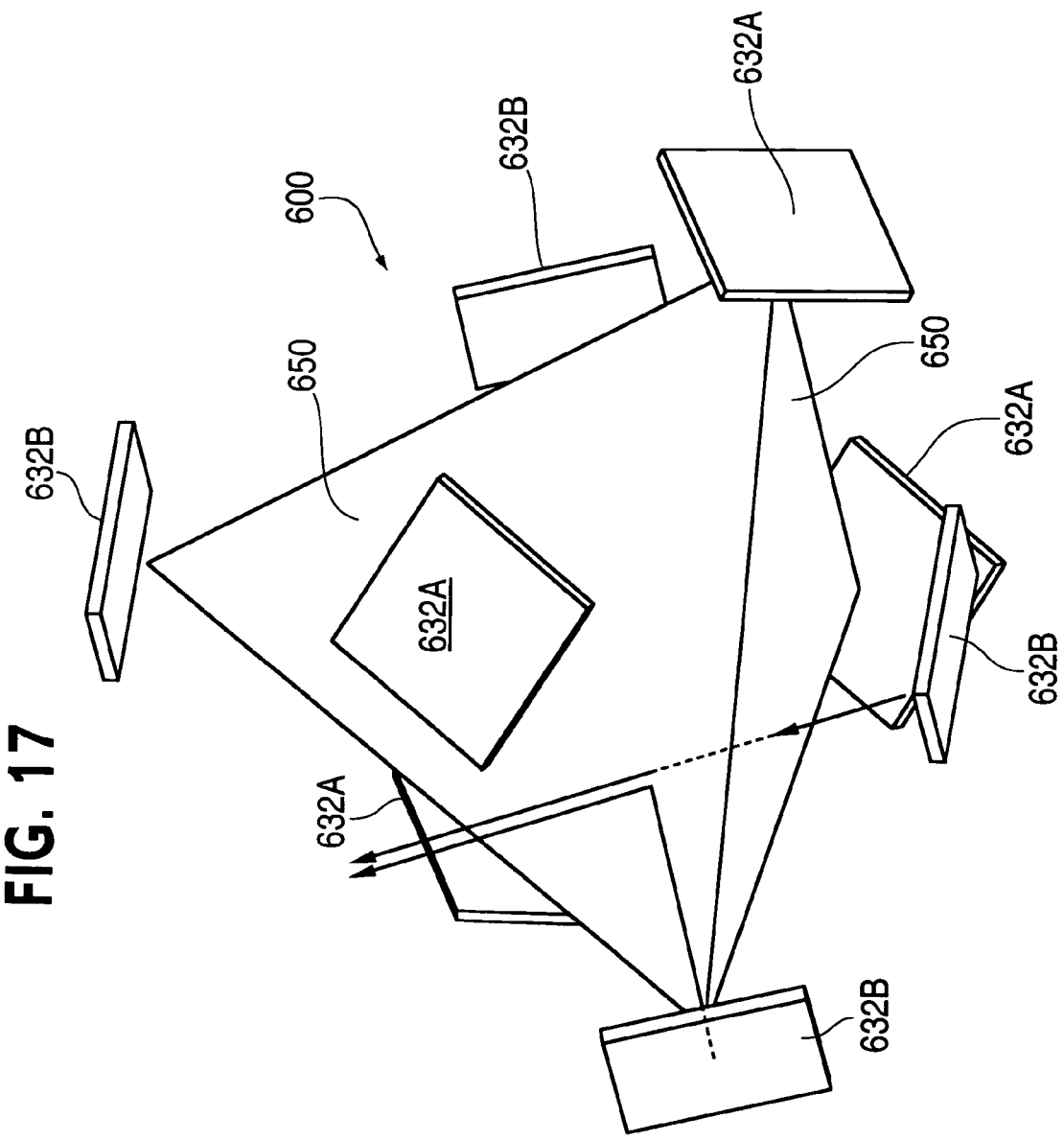
FIG. 17 is a perspective view of a ninth embodiment of the invention of eight solid state light emitting arrays facing four optical mixers arranged to face a structure with tetrahedral symmetry.

FIG. 17 illustrates a ninth embodiment 600 having four pairs of LED arrays 632A and 632B which face four optical mixers 650 configured in a structure with tetrahedral symmetry. It should be understood that the connections to a suitable controller and cooling system for the LED arrays, such as illustrated in FIG. 8, are not illustrated for purposes of simplifying the illustration. A solid line indicates light rays which are visible to the viewer and a dotted line indicates rays which are occluded from direct view.

Figure 18:
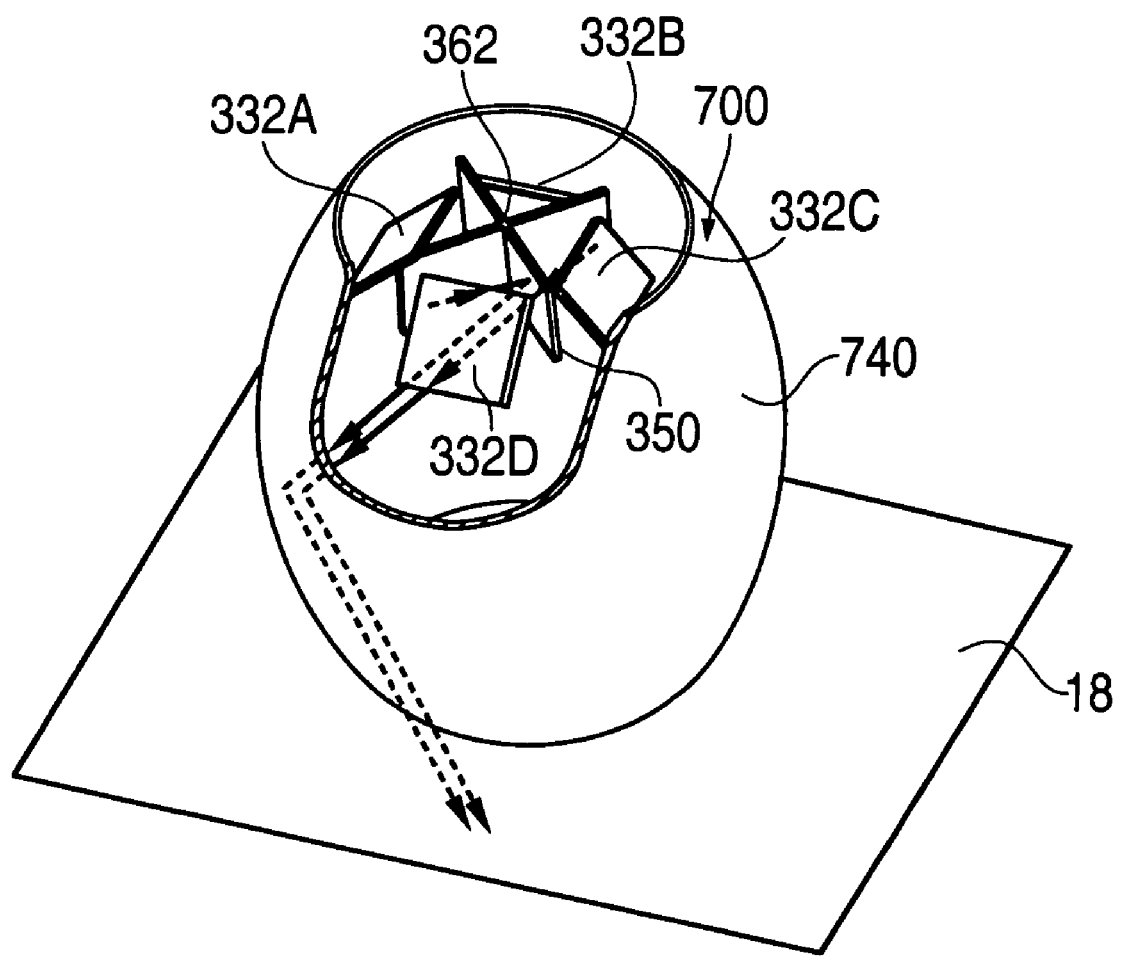
FIG. 18 is a perspective view of an tenth embodiment of the invention with four solid state light emitting arrays spaced between four intersecting optical mixing elements contained in an internal ellipsoidal reflector.

FIG. 18 shows a tenth embodiment 700 of the present invention having a configuration of four LED arrays 332A, 332B, 332C and 332D symmetrically disposed about four optical mixers 350 in a configuration similar to FIG. 11 except that an ellipsoidal reflector 740 is provided as the housing. The ellipsoid 740 has a major access, which is also the axis of rotation of the ellipse that sweeps out the surface of the ellipsoid, a minor axis, a first focus within the ellipsoid and a second focus outside the ellipsoid which are not illustrated. The LED radiation source is positioned on the major axis of the ellipsoid reflector 740 at the first focus. Since the irradiation source is extended, the image of the irradiation source will not be brought into sharp focus. As described above with respect to other embodiments, the internally reflective curved cylindrical housing, controller and cooling system have been omitted. A solid line indicates light rays which are visible to the viewer and a dotted line indicates rays which are occluded from direct view.

Figure 19:
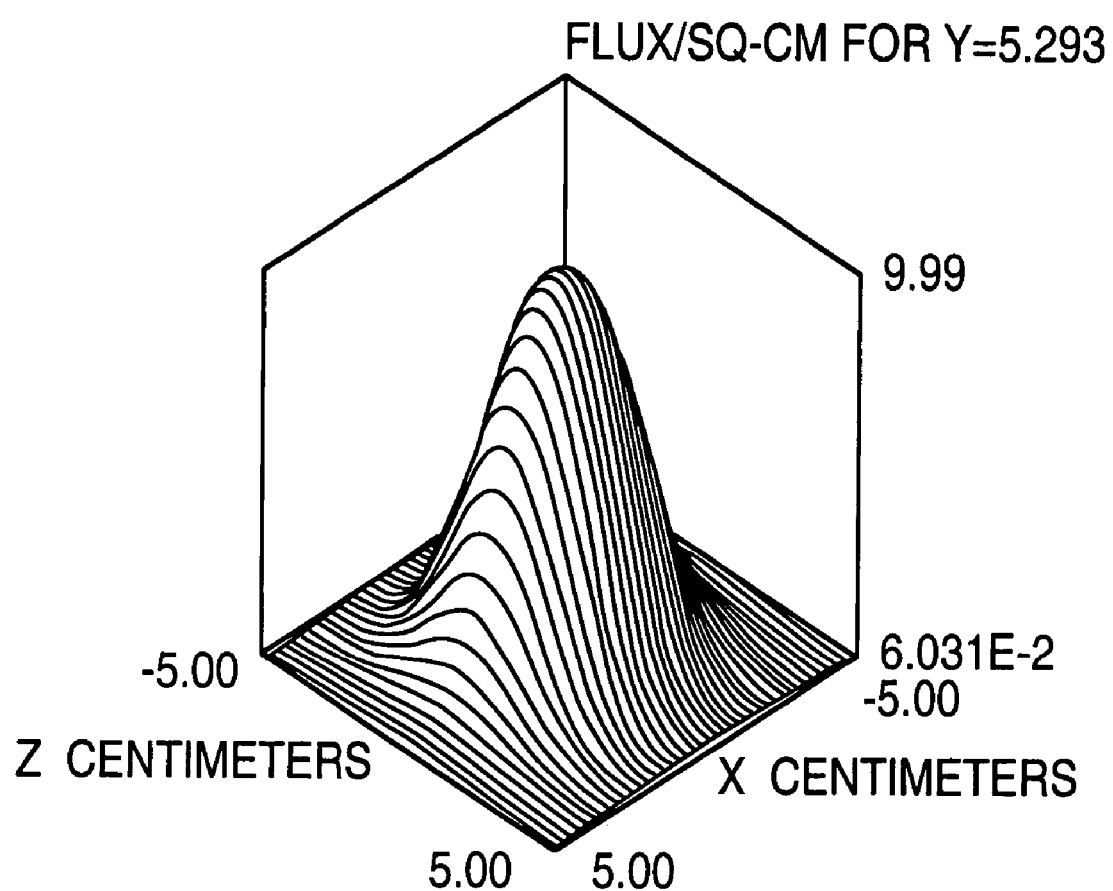
FIG. 19 shows the flux distribution of the ninth embodiment of FIG. 18.

FIG. 19 shows the simulated irradiance of the embodiment 700 of FIG. 18 on the irradiated surface 18. The radiance pattern of the beam shows a ring-like pattern near the peak irradiance. This pattern is due to the placement of the radiation sources 332A-332D in a circle about the optical mixers 350. As described above with respect to other embodiments, the internally reflective curved cylindrical housing, controller, cooling system and target surface have been emitted.

Figure 20:
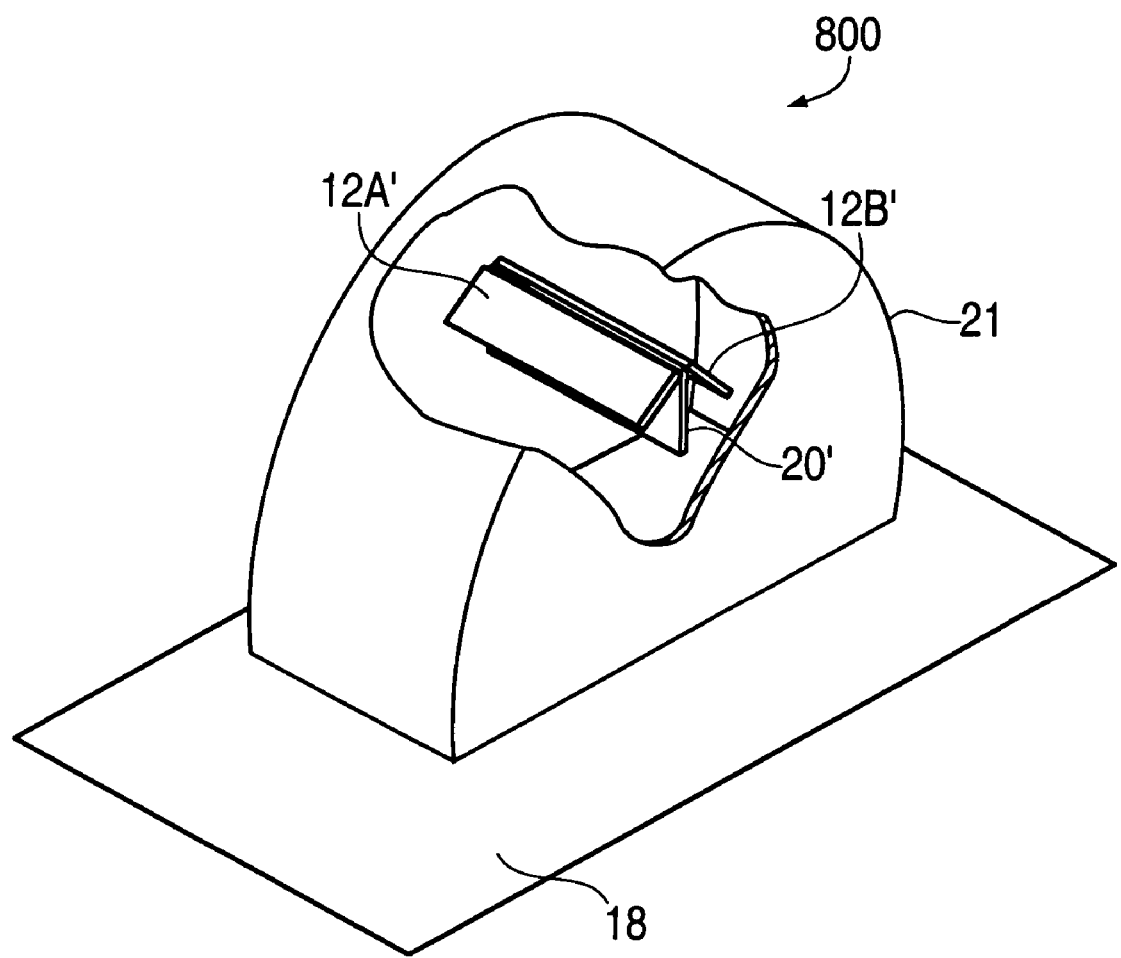
FIG. 20 is a perspective view of an eleventh embodiment of the invention with two elongated solid state light emitting arrays facing an optical mixer contained in an internally reflective elliptical reflector.
Figure 21:
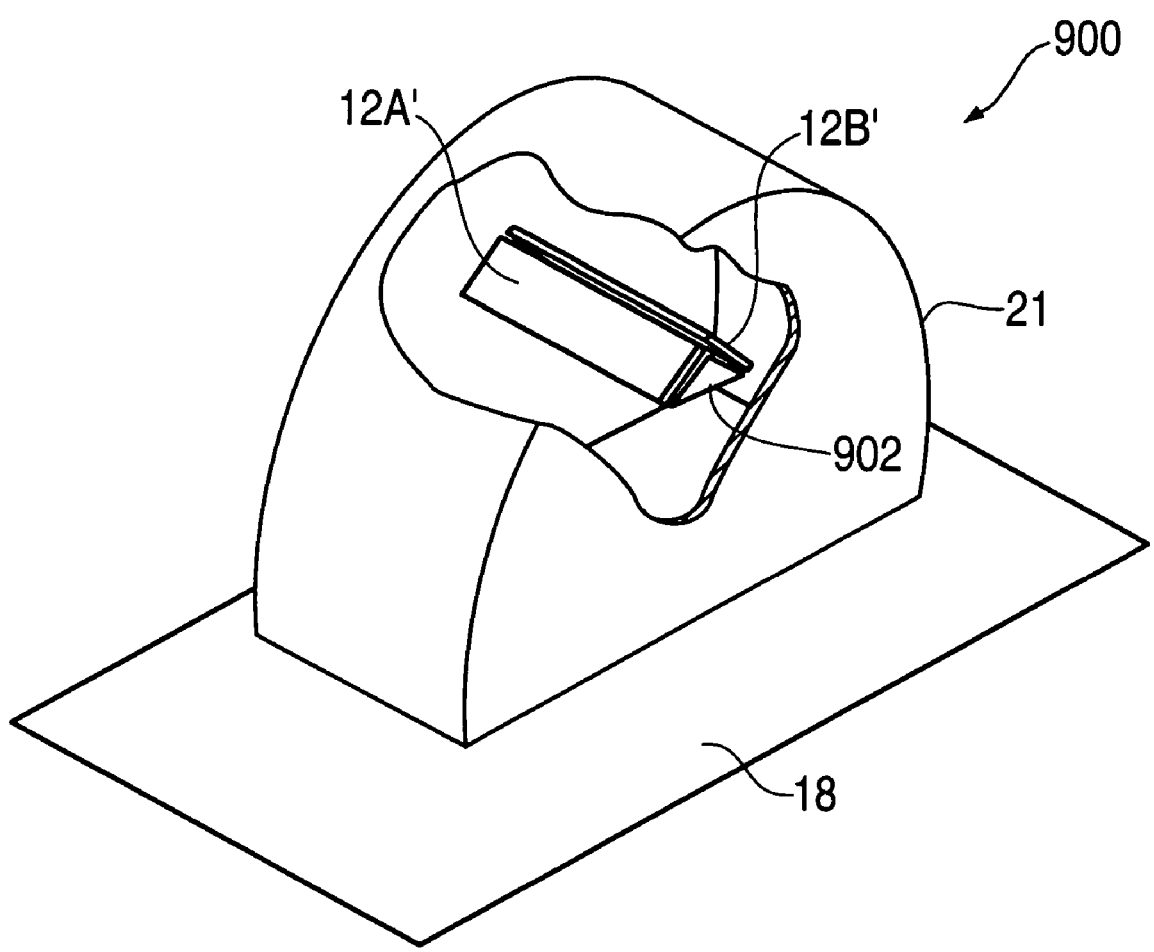
FIG. 21 is a perspective view of a twelfth embodiment of the invention with two elongated solid state light emitting arrays facing a prismatic mixing device contained in an elliptical reflector.

FIGS. 20 and 21 show eleventh and twelfth embodiments 800 and 900 of the present invention that utilize elongated linear arrays of diodes 12A' and 12B' with the embodiment 800 having elongated optical mixer 20' which is a semitransparent mirror and the embodiment 900 utilizing an optical mixer 902 which is a prism for splitting and mixing beams from the arrays 12A' and 12B' using internal reflection rather than reflection from a mirror. As described above with respect to other embodiments, the internally reflective curved cylindrical housing, controller and cooling system have been emitted.

Figure 22:
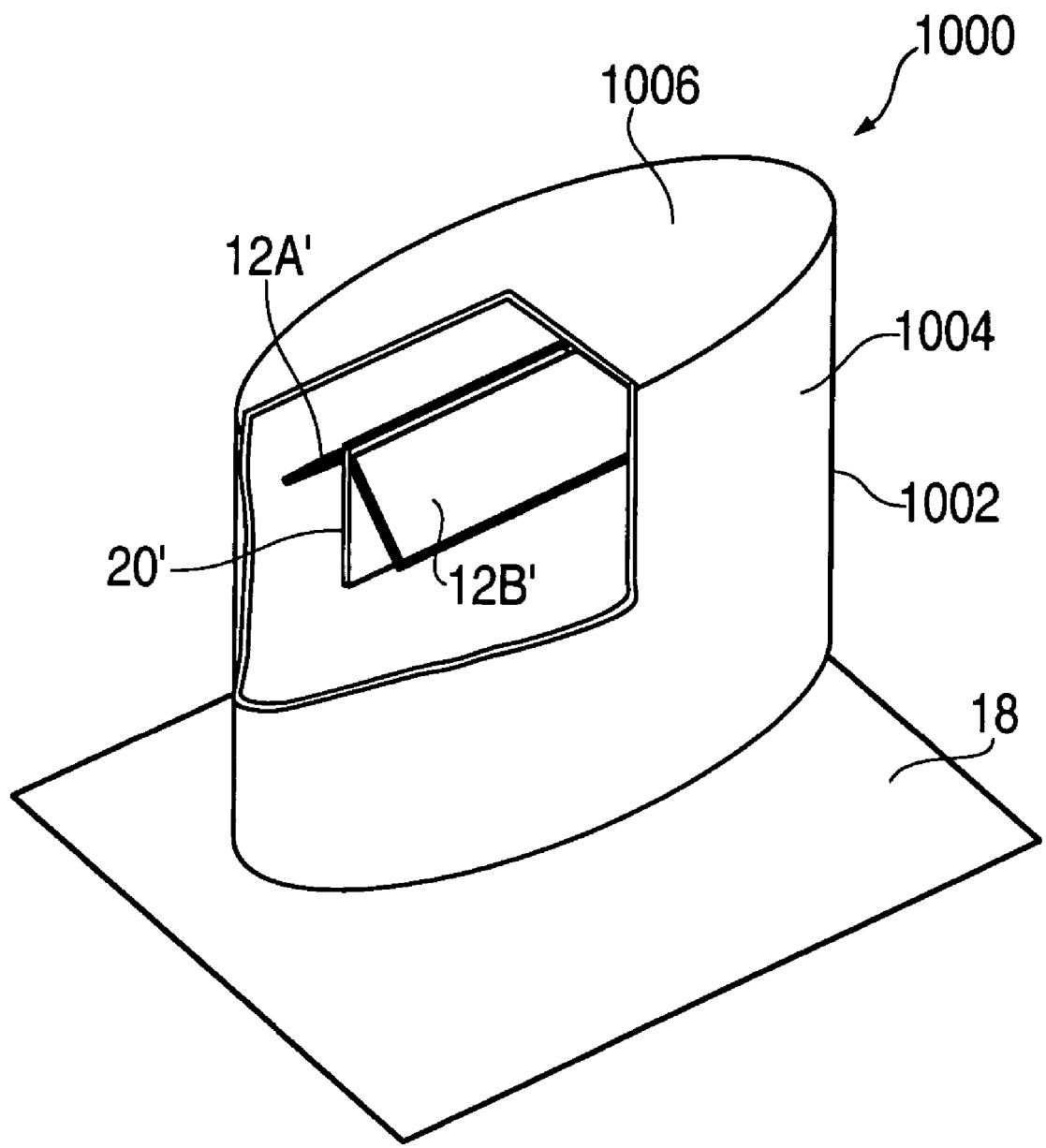
FIG. 22 is a perspective view of a thirteenth embodiment of the invention with two elongated solid state light emitting arrays facing one optical mixing element contained in a reflector with an elliptical cross section.

FIG. 22 shows a twelfth embodiment 1000 which is similar to the embodiment 800 of FIG. 20 regarding the configuration of the elongated light emitting diode arrays 12A' and 12B' and the elongated optical mixer 20'. The embodiment 1000 differs with regard to the curved internally reflective housing 1002 which is an elliptical reflector with a side reflector as an ellipse with semi-major and semi-minor axis being parallel and perpendicular to the optical mixer 20' or a prism such as 902 used in the embodiment 900 of FIG. 21 and replacement thereof. The side reflector 1004 is attached to an elliptical plate 1006 to form an elliptical housing. As described above with respect to other embodiments, the internally reflective curved cylindrical housing, controller, cooling system and target surface have been emitted.

While the invention has been described in terms of its preferred embodiments, it is intended that numerous modifications can be made thereto without departing from the spirit and scope of the invention as defined in the appended claims. It is intended that all such modifications fall within the scope of the appended claims.

What is claimed is:

1. A solid state light source comprising:
   at least three light emitting arrays, each array comprising solid state light emitters which are mounted so that each emitter emits light away from one side of a surface;
   at least three optical mixers, each of the at least three optical mixers being symmetrically positioned with respect to at least one pair of the at least three light emitting arrays, reflecting part of the light emitted from one of the at least one pair of symmetrically positioned arrays and transmitting part of the light emitted from another one of the at least one pair of symmetrically positioned arrays to mix the light from the at least one pair of symmetrically positioned arrays to produce mixed light which irradiates a surface; and a housing comprising an interior curved reflective surface, the housing containing the at least three light emitting arrays and the at least three optical mixers, and including an opening from which the mixed light is emitted and the interior curved reflective surface reflecting at least part of the light emitted from the one side of the arrays toward the surface.

2. A solid state light source in accordance with claim 1 wherein:
the at least three optical mixers comprise at least one prism.

3. A solid state light source in accordance with claim 1 comprising:
a controller, coupled to at least one of the at least three light emitting arrays, which controls a power level of light emitted from the at least one power-controlled array in at least one frequency band;
wherein the power level of the light emitted by the at least one power-controlled array in the at least one frequency band is chosen to provide a controlled power level of mixed light to irradiate the surface.

4. A solid state light source in accordance with claim 1 wherein:
the at least three optical mixers are joined together and the housing comprises an inward-facing reflective cylinder with a location at which the at least three optical mixers are joined together being located within the cylinder.

5. A solid state light source in accordance with claim 4 wherein:
the at least three optical mixers comprise at least one partially reflective mirror.

6. A solid state light source in accordance with claim 4 comprising:
a controller, coupled to at least one of the at least three light emitting arrays, which controls a power level of light emitted from the at least one power-controlled array in at least one frequency band;
wherein the power level of the light emitted by the at least one power-controlled array in the at least one frequency band is chosen to provide a controlled power level of mixed light to irradiate the surface.

7. A solid state light source in accordance with claim 1 wherein:
the at least three optical mixers comprise at least one partially reflective mirror.

8. A solid state light source in accordance with claim 7 wherein:
the at least one partially reflective mirror is approximately 50% reflective.

9. A solid state light source in accordance with claim 1 wherein:
the at least three optical mixers and the at least three light emitting arrays comprise four optical mixers and four light emitting arrays.

10. A solid state light source in accordance with claim 9 comprising:
a controller, coupled to at least one of the four light emitting arrays, which controls a power level of light emitted from the at least one power-controlled array in at least one frequency band;
wherein the power level of the light emitted by the at least one power-controlled array in the at least one frequency band is chosen to provide a controlled power level of mixed light to irradiate the surface.

11. A solid state light source in accordance with claim 9 wherein:
the four optical mixers are joined together and the housing comprises an inward-facing reflective cylinder with a location at which of the four optical mixers are joined together being located within the cylinder.

12. A solid state light source in accordance with claim 11 wherein:
the four optical mixers comprise at least one partially reflective mirror.

13. A solid state light source in accordance with claim 11 comprising:
a controller, coupled to at least one of the four light emitting arrays, which controls a power level of light emitted from the at least one power-controlled array in at least one frequency band;
wherein the power level of the light emitted by the at least one power-controlled array in the at least one frequency band is chosen to provide a controlled power level of mixed light to irradiate the surface.

14. A solid state light source in accordance with claim 9 wherein:
the four optical mixers comprise at least one partially reflective mirror.

15. A solid state light source in accordance with claim 14 wherein:
the at least one partially reflective mirror is approximately 50% reflective.

16. A solid state light source in accordance with claim 1 wherein:
the at least three optical mixers and the at least three light emitting arrays comprise six optical mixers and six light emitting arrays.

17. A solid state light source in accordance with claim 16 comprising:
a controller, coupled to at least one of the six light emitting arrays, which controls a power level of light emitted from the at least one power-controlled array in at least one frequency band;
wherein the power level of the light emitted by the at least one power-controlled array in the at least one frequency band is chosen to provide a controlled power level of mixed light to irradiate the surface.

18. A solid state light source in accordance with claim 16 wherein:
the six optical mixers are joined together and the housing comprises an inward-facing reflective cylinder with a location at which the six optical mixers are joined being located within the cylinder.

19. A solid state light source in accordance with claim 18 wherein:
the six optical mixers comprise at least one partially reflective mirror.

20. A solid state light source in accordance with claim 18 comprising:
a controller, coupled to at least one of the six light emitting arrays, which controls a power level of light emitted from the at least one power-controlled array in at least one frequency band;
wherein the power level of the light emitted by the at least one power-controlled array in the at least one frequency band is chosen to provide a controlled power level of mixed light to irradiate the surface.

21. A solid state light source in accordance with claim 16 wherein:
the six optical mixers comprise at least one partially reflective mirror.

22. A solid state light source in accordance with claim 21 wherein:
the at least one partially reflective mirror is approximately 50% reflective.

23. A solid state light source comprising:
at least two light emitting arrays, each array comprising solid state light emitters which are mounted so that each emitter emits light away from one side of a surface;
at least one optical mixer, each optical mixer being positioned symmetrically with respect to at least one pair of the arrays, reflecting part of the light emitted from one of the at least one pair of symmetrically positioned arrays and transmitting part of the light emitted from another one of the at least one pair of symmetrically positioned arrays to mix the light from the at least one pair of symmetrically positioned arrays to produce mixed light which irradiates a surface; and
a housing comprising an interior curved reflective surface, the housing containing the at least two light emitting arrays and the at least one optical mixer, and including an opening from which the mixed light is emitted and the interior curved reflective surface reflecting at least part of the light emitted from the one side of the arrays toward the surface;
wherein the at least one optical mixer comprises a partially reflective mirror which is less than 40% reflective.

24. A method of irradiating a target surface with a solid state light source including at least three light emitting arrays, each array comprising solid state light emitters which are mounted so that each emitter emits light away from one side of a surface, at least three optical mixers, each optical mixer being positioned symmetrically with respect to at least one pair of the at least three light emitting arrays, reflecting part of the light emitted from one of the at least one pair of symmetrically positioned arrays and transmitting part of the light emitted from another one of the at least one pair of symmetrically positioned arrays to mix the light from the at least one pair of symmetrically positioned arrays to produce mixed light, a housing comprising an interior curved reflective surface, the housing containing the at least three light emitting arrays and the at least three optical mixers and an opening from which the mixed light is emitted and the interior curved reflective surface reflecting at least part of the light emitted from the one side of the arrays to the target surface, the method comprising:
positioning the target surface to be irradiated with the mixed light emitted from the opening.

25. A method in accordance with claim 24 wherein:
the at least three optical mixers comprise at least one prism.

26. A method in accordance with claim 24 wherein the solid state light source further comprises a controller, coupled to at least one of the at least three light emitting arrays, which controls a power level of light emitted from the at least one power-controlled array in at least one frequency band, the method further comprising:
controlling the power level of light emitted from the at least one power-controlled array in the at least one frequency band to provide a controlled power level of mixed light to irradiate the target surface.

27. A method in accordance with claim 24 wherein:
the at least three optical mixers and the at least three light emitting arrays comprise four optical mixers and four light emitting arrays.

28. A method in accordance with claim 27 wherein the solid state light source further comprises a controller, coupled to at least one of the four light emitting arrays, which controls a power level of light emitted from the at least one power-controlled array in at least one frequency band, the method further comprising:
controlling the power level of light emitted from the at least one power-controlled array in the at least one frequency band to provide a controlled power level of mixed light to irradiate the target surface.

29. A method in accordance with claim 27 wherein:
the four optical mixers comprise at least one partially reflective mirror.

30. A method in accordance with claim 29 wherein:
the partially reflective mirror is approximately 50% reflective.

31. A method in accordance with claim 27 wherein:
the four optical mixers are joined together and the housing comprises an inward-facing reflective cylinder with a location at which of the four optical mixers are joined together being located within the cylinder.

32. A method in accordance with claim 31 wherein the solid state light source further comprises a controller, coupled to at least one of the four light emitting arrays, which controls a power level of light emitted the from at least one power-controlled array in at least one frequency band, the method further comprising:
controlling the power level of light emitted from the at least one power-controlled array in the at least one frequency band to provide a controlled power level of mixed light to irradiate the target surface.

33. A method in accordance with claim 31 wherein:
the four optical mixers comprise at least one partially reflective mirror.

34. A method in accordance with claim 24 wherein:
the at least three optical mixers and the at least three light emitting arrays comprise six optical mixers and six light emitting arrays.

35. A method in accordance with claim 34 wherein the solid state light source further comprises a controller, coupled to at least one of the six light emitting arrays, which controls a power level of light emitted from the at least one power-controlled array in at least one frequency band, the method further comprising:
controlling the power level of light emitted from the at least one power-controlled array in the at least one frequency band to provide a controlled power level of mixed light to irradiate the target surface.

36. A method in accordance with claim 34 wherein:
the six optical mixers comprise at least one partially reflective mirror.

37. A method in accordance with claim 36 wherein:
the partially reflective mirror is approximately 50% reflective.

38. A method in accordance with claim 34 wherein:
the six optical mixers are joined together and the housing comprises an inward-facing reflective cylinder with a location at which the six optical mixers are joined being located within the cylinder.

39. A method in accordance with claim 38 wherein the solid state light source further comprises a controller, coupled to at least one of the six light emitting arrays, which controls a power level of light emitted the from at least one power-controlled array in at least one frequency band, the method further comprising:
controlling the power level of light emitted from the at least one power-controlled array in the at least one frequency band to provide a controlled power level of mixed light to irradiate the target surface.

40. A method in accordance with claim 38 wherein:
the six optical mixers comprise at least one partially reflective mirror.

41. A method in accordance with claim 24 wherein:
the at least three optical mixers are joined together and the housing comprises an inward-facing reflective cylinder with a location at which the three optical mixers are joined together being located within the cylinder.

42. A method in accordance with claim 41 wherein the solid state light source further comprises a controller, coupled to at least one of the at least three light emitting arrays, which controls a power level of light emitted the from at least one power-controlled array in at least one frequency band, the method further comprising:
controlling the power level of light emitted from the at least one power-controlled array in the at least one frequency band to provide a controlled power level of mixed light to irradiate the target surface.

43. A method in accordance with claim 41 wherein:
the at least three optical mixers comprise at least one partially reflective mirror.

44. A method in accordance with claim 24 wherein:
the at least three optical mixers comprise at least one partially reflective mirror.

45. A method in accordance with claim 44 wherein:
the partially reflective mirror is approximately 50% reflective.

46. A method of irradiating a target surface with a solid state light source including at least two light emitting arrays, each array comprising solid state light emitters which are mounted so that each emitter emits light away from one side of a surface, at least one optical mixer, each optical mixer being positioned symmetrically with respect to at least one pair of the arrays, reflecting part of the light emitted from one of the at least one pair of symmetrically positioned arrays and transmitting part of the light emitted from another one of the at least one pair of symmetrically positioned arrays to mix the light from the at least one pair of symmetrically positioned arrays to produce mixed light, a housing comprising an interior curved reflective surface, the housing containing the at least two light emitting arrays and the at least one optical mixer and an opening from which the mixed light is emitted and the interior curved reflective surface reflecting at least some of the light emitted from the one side of the arrays to the target surface, the method comprising:
positioning the target surface to be irradiated with the mixed light emitted from the opening;
wherein the at least one optical mixer comprises a partially reflective mirror which is less than 40% reflective.

* * * * *